US009687200B2

(12) United States Patent
Maurer, Jr.

(10) Patent No.: US 9,687,200 B2
(45) Date of Patent: Jun. 27, 2017

(54) RADIATION TREATMENT DELIVERY SYSTEM WITH TRANSLATABLE RING GANTRY

(75) Inventor: Calvin R. Maurer, Jr., San Jose, CA (US)

(73) Assignee: Accuray Incorporated, Sunnyvale, CA (US)

(*) Notice: Subject to any disclaimer, the term of this patent is extended or adjusted under 35 U.S.C. 154(b) by 383 days.

(21) Appl. No.: 13/088,289

(22) Filed: Apr. 15, 2011

(65) Prior Publication Data
US 2011/0301449 A1    Dec. 8, 2011

Related U.S. Application Data

(60) Provisional application No. 61/434,824, filed on Jan. 20, 2011.

(51) Int. Cl.
*A61B 5/055* (2006.01)
*A61B 6/03* (2006.01)
(Continued)

(52) U.S. Cl.
CPC .......... *A61B 6/032* (2013.01); *A61N 5/1049* (2013.01); *A61B 5/055* (2013.01); *A61B 6/4085* (2013.01);
(Continued)

(58) Field of Classification Search
None
See application file for complete search history.

(56) References Cited
U.S. PATENT DOCUMENTS 2,890,349 A * 6/1959 Huszar ............................ 378/65

2,950,394 A    8/1960 Stava et al.
(Continued)

FOREIGN PATENT DOCUMENTS

DE    102008030893    12/2009
EP    1 419 801    5/2004
(Continued)

OTHER PUBLICATIONS

Kilby et al., "The CyberKnife® Robotic Radiosurgery System in 2010", Tech. In Cancer Res. And Treatment vol. 9, no. 5, pp. 433-452 (2010).
(Continued)

*Primary Examiner* — Long V Le
*Assistant Examiner* — Bradley Impink
(74) *Attorney, Agent, or Firm* — Womble Carlyle Sandridge & Rice LLP

(57) ABSTRACT

Systems, methods, and related computer program products for image-guided radiation treatment (IGRT) are described. For one preferred embodiment, an IGRT apparatus is provided comprising a ring gantry having a central opening and a radiation treatment head coupled to the ring gantry that is rotatable around the central opening in at least a 180 degree arc. For one preferred embodiment, the apparatus further comprises a gantry translation mechanism configured to translate the ring gantry in a direction of a longitudinal axis extending through the central opening. Noncoplanar radiation treatment delivery can thereby be achieved without requiring movement of the patient. For another preferred embodiment, an independently translatable 3D imaging device distinct from the ring gantry is provided for further achieving at least one of pre-treatment imaging and setup imaging of the target tissue volume without requiring movement of the patient.

7 Claims, 15 Drawing Sheets

(51) Int. Cl.
*A61N 5/10* (2006.01)
*G01N 23/04* (2006.01)
*A61B 6/00* (2006.01)

(52) U.S. Cl.
CPC ..... *A61B 6/4405* (2013.01); *A61N 2005/1062* (2013.01)

(56) References Cited

U.S. PATENT DOCUMENTS

| | | | |
|---|---|---|---|
| 3,466,439 A | 9/1969 | Edvard | |
| 4,651,007 A | 3/1987 | Perusek et al. | |
| 5,027,818 A * | 7/1991 | Bova et al. | 600/427 |
| 5,099,134 A | 3/1992 | Hase | |
| 5,189,687 A * | 2/1993 | Bova et al. | 378/65 |
| 5,305,368 A * | 4/1994 | Bisek | A61B 6/032 378/146 |
| 5,380,336 A * | 1/1995 | Misko et al. | 606/130 |
| 5,464,013 A | 11/1995 | Lemelson | |
| 5,485,502 A * | 1/1996 | Hinton | A61B 6/102 250/363.01 |
| 5,634,929 A * | 6/1997 | Misko et al. | 606/130 |
| 5,638,419 A * | 6/1997 | Ingwersen | A61B 6/032 378/195 |
| 5,724,400 A * | 3/1998 | Swerdloff et al. | 378/65 |
| 5,818,902 A | 10/1998 | Yu | |
| 6,075,840 A | 6/2000 | Pellegrino | |
| 6,269,143 B1 * | 7/2001 | Tachibana | 378/65 |
| RE37,474 E | 12/2001 | Hug et al. | |
| 6,385,288 B1 | 5/2002 | Kanematsu | |
| 6,435,713 B1 * | 8/2002 | Iizuka | A61B 6/032 378/195 |
| 6,501,981 B1 | 12/2002 | Schweikard et al. | |
| 6,614,871 B1 | 9/2003 | Kobiki et al. | |
| 6,647,092 B2 | 11/2003 | Eberhard | |
| 6,778,850 B1 | 8/2004 | Adler | |
| 6,865,254 B2 * | 3/2005 | Nafstadius | 378/65 |
| 6,885,724 B2 | 4/2005 | Li | |
| 6,969,194 B1 * | 11/2005 | Nafstadius | 378/197 |
| 6,973,158 B2 | 12/2005 | Besson | |
| 6,973,202 B2 | 12/2005 | Mostafavi | |
| 6,977,987 B2 * | 12/2005 | Yamashita et al. | 378/64 |
| 7,085,347 B2 * | 8/2006 | Mihara et al. | 378/65 |
| 7,142,633 B2 | 11/2006 | Eberhard | |
| 7,162,008 B2 | 1/2007 | Earl | |
| 7,188,999 B2 * | 3/2007 | Mihara et al. | 378/197 |
| 7,193,227 B2 * | 3/2007 | Hiramoto et al. | 250/492.3 |
| 7,204,640 B2 | 4/2007 | Fu | |
| 7,212,608 B2 * | 5/2007 | Nagamine et al. | 378/65 |
| 7,212,609 B2 * | 5/2007 | Nagamine et al. | 378/65 |
| 7,218,702 B2 | 5/2007 | Mistretta et al. | |
| 7,227,925 B1 * | 6/2007 | Mansfield et al. | 378/65 |
| 7,231,017 B2 | 6/2007 | Gertsenshteyn | |
| 7,239,684 B2 | 7/2007 | Hara et al. | |
| 7,245,698 B2 | 7/2007 | Pang et al. | |
| 7,246,943 B2 | 7/2007 | Gotoh | |
| 7,265,356 B2 | 9/2007 | Pelizzari et al. | |
| 7,302,033 B2 | 11/2007 | Carrano | |
| 7,345,282 B2 | 3/2008 | Hawman | |
| 7,349,730 B2 * | 3/2008 | Ein-Gal | 600/427 |
| 7,388,940 B1 | 6/2008 | De Man | |
| 7,405,407 B2 * | 7/2008 | Hiramoto et al. | 250/370.09 |
| 7,436,928 B2 * | 10/2008 | Urano et al. | 378/65 |
| 7,440,603 B2 | 10/2008 | Eberhard | |
| 7,444,011 B2 | 10/2008 | Pan et al. | |
| 7,446,328 B2 | 11/2008 | Rigney | |
| 7,471,765 B2 | 12/2008 | Jaffray et al. | |
| 7,505,562 B2 | 3/2009 | Dinca et al. | |
| 7,519,149 B2 * | 4/2009 | Mackie et al. | 378/65 |
| 7,519,151 B1 * | 4/2009 | Shukla et al. | 378/65 |
| 7,532,705 B2 | 5/2009 | Yin et al. | |
| 7,545,911 B2 * | 6/2009 | Rietzel et al. | 378/65 |
| 7,564,945 B2 * | 7/2009 | Kim | 378/65 |
| 7,567,647 B1 | 7/2009 | Maltz | |
| 7,577,233 B1 | 8/2009 | Tsang et al. | |
| 7,623,623 B2 | 11/2009 | Raanes | |
| 7,639,777 B2 | 12/2009 | Warner | |
| 7,639,853 B2 * | 12/2009 | Olivera et al. | 382/128 |
| 7,640,607 B2 * | 1/2010 | Guertin et al. | 5/601 |
| 7,657,304 B2 * | 2/2010 | Mansfield et al. | 600/427 |
| 7,668,292 B1 * | 2/2010 | Bose et al. | 378/65 |
| 7,672,429 B2 * | 3/2010 | Urano et al. | 378/65 |
| 7,679,073 B2 * | 3/2010 | Urano et al. | 250/505.1 |
| 7,684,647 B2 | 3/2010 | Fu et al. | |
| 7,693,257 B2 | 4/2010 | Allison | |
| 7,711,087 B2 * | 5/2010 | Mostafavi | 378/65 |
| 7,801,269 B2 * | 9/2010 | Cravens et al. | 378/65 |
| 7,831,013 B2 | 11/2010 | Star-Lack et al. | |
| 7,876,881 B2 | 1/2011 | Jeffery | |
| 7,902,530 B1 * | 3/2011 | Sahadevan | 250/494.1 |
| 7,961,838 B2 * | 6/2011 | Yin | 378/5 |
| 7,983,380 B2 * | 7/2011 | Guertin et al. | 378/4 |
| 8,130,907 B2 * | 3/2012 | Maurer et al. | 378/65 |
| 8,254,521 B2 | 8/2012 | Brooks et al. | |
| 8,559,596 B2 | 10/2013 | Thomson et al. | |
| 2002/0154728 A1 | 10/2002 | Morita et al. | |
| 2003/0048868 A1 | 3/2003 | Bailey et al. | |
| 2004/0005027 A1 * | 1/2004 | Nafstadius | 378/65 |
| 2004/0037390 A1 * | 2/2004 | Mihara et al. | 378/65 |
| 2004/0170254 A1 * | 9/2004 | Gregerson | A61B 6/032 378/197 |
| 2004/0184579 A1 * | 9/2004 | Mihara et al. | 378/65 |
| 2004/0184583 A1 * | 9/2004 | Nagamine et al. | 378/209 |
| 2005/0049478 A1 | 3/2005 | Kuduvalli et al. | |
| 2005/0078861 A1 | 4/2005 | Usikov | |
| 2005/0117708 A1 | 6/2005 | Cho | |
| 2005/0226364 A1 | 10/2005 | De Man | |
| 2006/0002509 A1 | 1/2006 | Claus et al. | |
| 2006/0008047 A1 | 1/2006 | Zhou | |
| 2006/0098855 A1 | 5/2006 | Gkanatsios et al. | |
| 2006/0163495 A1 * | 7/2006 | Hiramoto et al. | 250/492.3 |
| 2006/0173294 A1 * | 8/2006 | Ein-Gal | 600/427 |
| 2006/0203958 A1 * | 9/2006 | Nagamine et al. | 378/20 |
| 2006/0210015 A1 | 9/2006 | Pelc | |
| 2007/0003010 A1 | 1/2007 | Guertin et al. | |
| 2007/0003123 A1 | 1/2007 | Fu | |
| 2007/0014391 A1 | 1/2007 | Mostafavi et al. | |
| 2007/0016014 A1 * | 1/2007 | Hara et al. | 600/426 |
| 2007/0025509 A1 | 2/2007 | Pang et al. | |
| 2007/0041500 A1 * | 2/2007 | Olivera et al. | 378/65 |
| 2007/0076846 A1 | 4/2007 | Ruchala | |
| 2007/0116175 A1 | 5/2007 | Zhang et al. | |
| 2007/0195930 A1 * | 8/2007 | Kapatoes et al. | 378/65 |
| 2007/0211856 A1 * | 9/2007 | Urano et al. | 378/65 |
| 2007/0211857 A1 * | 9/2007 | Urano et al. | 378/65 |
| 2007/0237290 A1 | 10/2007 | Mostafavi | |
| 2007/0242801 A1 * | 10/2007 | Mackie et al. | 378/65 |
| 2007/0253523 A1 * | 11/2007 | Zamyatin | 378/4 |
| 2007/0291895 A1 | 12/2007 | Yin et al. | |
| 2007/0297566 A1 * | 12/2007 | Urano et al. | 378/65 |
| 2008/0056435 A1 | 3/2008 | Basu et al. | |
| 2008/0071420 A1 | 3/2008 | Guertin et al. | |
| 2008/0083871 A1 * | 4/2008 | Cravens et al. | 250/252.1 |
| 2008/0101669 A1 * | 5/2008 | Jeung | 382/128 |
| 2008/0130825 A1 | 6/2008 | Fu et al. | |
| 2008/0170663 A1 * | 7/2008 | Urano et al. | 378/65 |
| 2008/0197303 A1 * | 8/2008 | Aoi et al. | 250/522.1 |
| 2008/0197304 A1 * | 8/2008 | Urano et al. | 250/522.1 |
| 2008/0240350 A1 | 10/2008 | Moyers | |
| 2008/0260093 A1 | 10/2008 | Bontus | |
| 2009/0003512 A1 * | 1/2009 | Pouliot et al. | 378/4 |
| 2009/0003522 A1 * | 1/2009 | Chien et al. | 378/65 |
| 2009/0003523 A1 | 1/2009 | Raanes et al. | |
| 2009/0074134 A1 | 3/2009 | Jeffrey | |
| 2009/0080603 A1 | 3/2009 | Shukla et al. | |
| 2009/0110145 A1 * | 4/2009 | Lu et al. | 378/65 |
| 2009/0110238 A1 | 4/2009 | Li | |
| 2009/0116616 A1 * | 5/2009 | Lu et al. | 378/65 |
| 2009/0175562 A1 | 7/2009 | Pan et al. | |
| 2009/0180666 A1 | 7/2009 | Sheng | |
| 2009/0189591 A1 | 7/2009 | Lu | |
| 2009/0226060 A1 * | 9/2009 | Gering et al. | 382/128 |
| 2009/0252291 A1 * | 10/2009 | Lu et al. | 378/65 |
| 2009/0296886 A1 | 12/2009 | Maltz et al. | |

(56) References Cited

U.S. PATENT DOCUMENTS

| | | |
|---|---|---|
| 2009/0297011 A1 | 12/2009 | Brunner |
| 2010/0020931 A1 | 1/2010 | Otto |
| 2010/0040197 A1* | 2/2010 | Maniawski et al. ............ 378/65 |
| 2010/0053208 A1* | 3/2010 | Menningen et al. ......... 345/619 |
| 2010/0054409 A1* | 3/2010 | Bose et al. ...................... 378/65 |
| 2010/0067739 A1 | 3/2010 | Mostafavi |
| 2010/0069742 A1 | 3/2010 | Partain |
| 2010/0091938 A1 | 4/2010 | Fadler |
| 2010/0104068 A1* | 4/2010 | Kilby et al. ..................... 378/65 |
| 2010/0128839 A1 | 5/2010 | Partain |
| 2010/0150304 A1* | 6/2010 | Kawamura ............ A61B 6/032 378/9 |
| 2010/0172468 A1* | 7/2010 | Gregerson ....................... 378/20 |
| 2010/0176309 A1* | 7/2010 | Mackie et al. ............. 250/492.3 |
| 2010/0228116 A1* | 9/2010 | Lu et al. ........................ 600/411 |
| 2010/0246767 A1* | 9/2010 | Tanabe ............................ 378/65 |
| 2011/0154569 A1* | 6/2011 | Wiggers ............... A61B 6/0407 5/81.1 R |
| 2011/0210261 A1* | 9/2011 | Maurer, Jr. .................... 250/393 |
| 2011/0211665 A1* | 9/2011 | Maurer et al. ..................... 378/9 |
| 2011/0313231 A1 | 12/2011 | Guertin et al. |
| 2012/0189102 A1* | 7/2012 | Maurer et al. ................... 378/65 |
| 2012/0330087 A1* | 12/2012 | Gregerson ......................... 600/7 |
| 2013/0101082 A1* | 4/2013 | Jordan et al. ................... 378/19 |

FOREIGN PATENT DOCUMENTS

| | | |
|---|---|---|
| EP | 1419799 | 5/2004 |
| EP | 1946795 | 7/2008 |
| EP | 2058027 | 5/2009 |
| EP | 1472702 | 12/2009 |
| WO | WO 00/74779 | 12/2000 |
| WO | WO 2008/106484 | 9/2008 |
| WO | 2009/012453 | 1/2009 |
| WO | 2010/030397 | 3/2010 |
| WO | WO 2011/106433 | 9/2011 |

OTHER PUBLICATIONS

Beavis "Is tomotherapy the future of IMRT?", The British J. of Radiology 77, pp. 285-295 (2004).

Court et al., "Evaluation of mechanical precision and alignment uncertainties for an itegrated CT/LINAC system", Med. Phys. vol. 30, No. 6, pp. 1198-1210 (2003).

Jaffray et al. "Flat-panel cone-beam computed tomography for image-guided radiation therapy", Int. J. Rad. Oncology Biol. Phys. vol. 53, No. 5, pp. 1337-1349 (2002).

Kuriyama et al., "A new irradiation unit constructed of self-moving gantry-CT and LINAC", Int. J. Rad. Oncology Biol. Phys. vol. 55, No. 2, pp. 428-435 (2003).

Mackie et al., "Image guidance for precise conformal radiogtherapy", Int. J. Radiation Oncology Biol. Phys. vol. 56, No. 1, pp. 89-105(2003).

Raaymakers et al., "Integrating a MRI scanner with a 6 MV radiotherapy accelerator: dose deposition in a transverse magnetic field", Phys. Med. Biol. vol. 49, pp. 4109-1418 (2004).

Uematsu et al., "A dual computed tomography linear accelerator unit for stereotactic radiation therapy: a new approach without cranially fixated stereotactic frames", Int. J. Rad. Oncology Biol. Phys. vol. 35, No. 3, pp. 587-592 (1996).

International Search Report for PCT/US2012/020795, mailed 7/13/12, 7 pgs.

International Preliminary Report on Patentability for PCT Application No. PCT/US2012/020795, filed Jan. 10, 2012, 9 pages.

International Search Report and Written Opinion for PCT Application No. PCT/US2012/020795, filed Jan. 10, 2012, 14 pages.

USPTO, Non-Final Office Action for U.S. Appl. No. 13/033,571 mailed on Jun. 26, 2013, 26 pages.

USPTO, Final Office Action for U.S. Appl. No. 13/033,571 mailed on Feb. 3, 2014, 17 pages.

USPTO, Notice of Allowance for U.S. Appl. No. 13/033,571 mailed on May 9, 2014.

USPTO, Non-Final Office Action for U.S. Appl. No. 13/033,584 mailed on Jan. 29, 2014, 19 pages.

USPTO, Notice of Allowance for U.S. Appl. No. 13/033,584 mailed on May 8, 2014.

International Search Report and Written Opinion for PCT Application No. PCT/US2012/020792, mailed Jul. 13, 2012.

International Preliminary Report on Patentability for PCT Application No. PCT/US2011/025936, mailed Aug. 1, 2013.

Kamino, Y., et. al., "Development of a Four-Dimensional Image-Guided Radiotherapy System With a Gimbaled X-Ray Head," Int. J. Radiation Oncology Bioi. Phys., vol. 66, No. 1, pp. 271-278 (2006).

Hirai et al., "State-of-the-Art Medical Treatment Machine MHI-TM2000", https://www.mhi.co.jp/technology/review/pdf/e461/e461029.pdf, Mitsubishi Heavy Industries Technical Review, 46(1)29-32, Mar. 2009.

GE Healthcare, "OEC 9900 Elite Premium Digital Mobile C-arm: Technical Data", <http://www.brown-heim.com/downloads/9790%20-%20NWH%20OR%20Bid%20Pack%202/Specifications/Volume%202/Individual%20files/XRA-01.pdf>, 7 pages, Accessed Jun. 28, 2016.

Siemens Healthcare, "ONCOR Digital Medical Linear Accelerator Specifications", <http://www.siemens.com.tr/i/assets/saglik/onkoloji/oncor.pdf>, 28 pages, Accessed Jun. 28, 2016.

Toshiba Electron Tubes & Devices Co., Ltd., "Toshiba X-Ray Tube: Product Information", <http://www.toshiba-tetd.co.jp/eng/product/read_binary.php?cid=100200200000&pid=20140730_1070&fn=PE-D-063_R_S_SR.pdf>, 10 pages, Accessed Jun. 28, 2016.

Medtronic, "O-ARM: Complete Multidimensional Surgical Imaging System: Technical Guide", <http://www.medtronicbrasil.com.br/wcm/groups/mdtcom_sg/@mdt/@navigation/documents/documents/9670866-pa_2010012916392511.pdf>, 6 pages, Accessed Jun. 28, 2016.

* cited by examiner

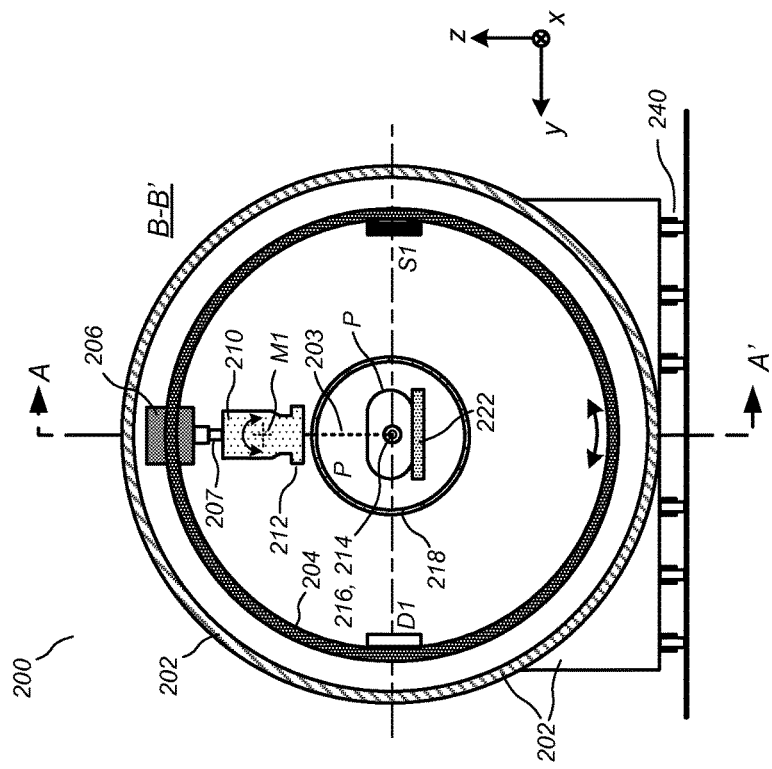
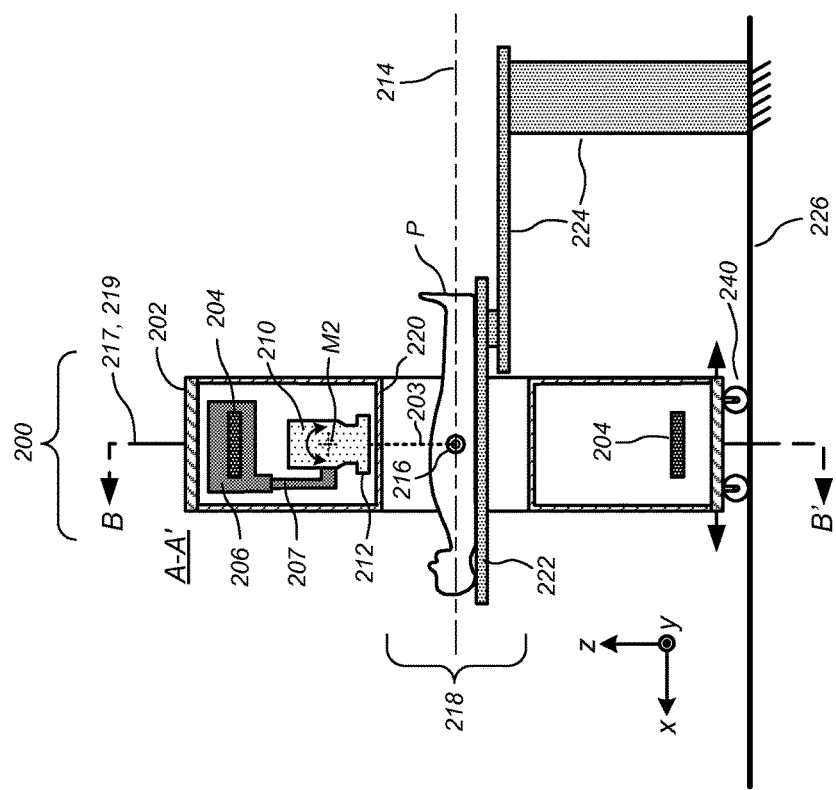
FIG. 2B
FIG. 2A

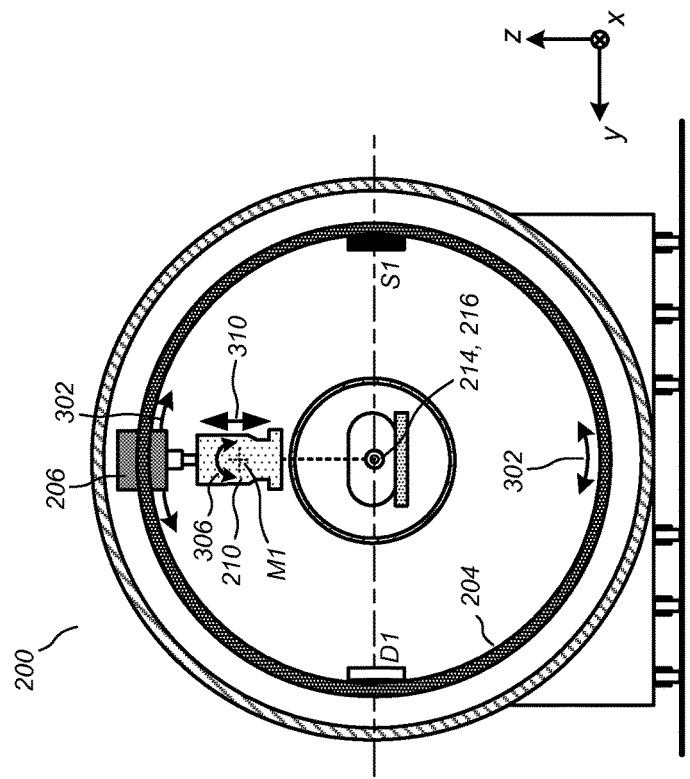
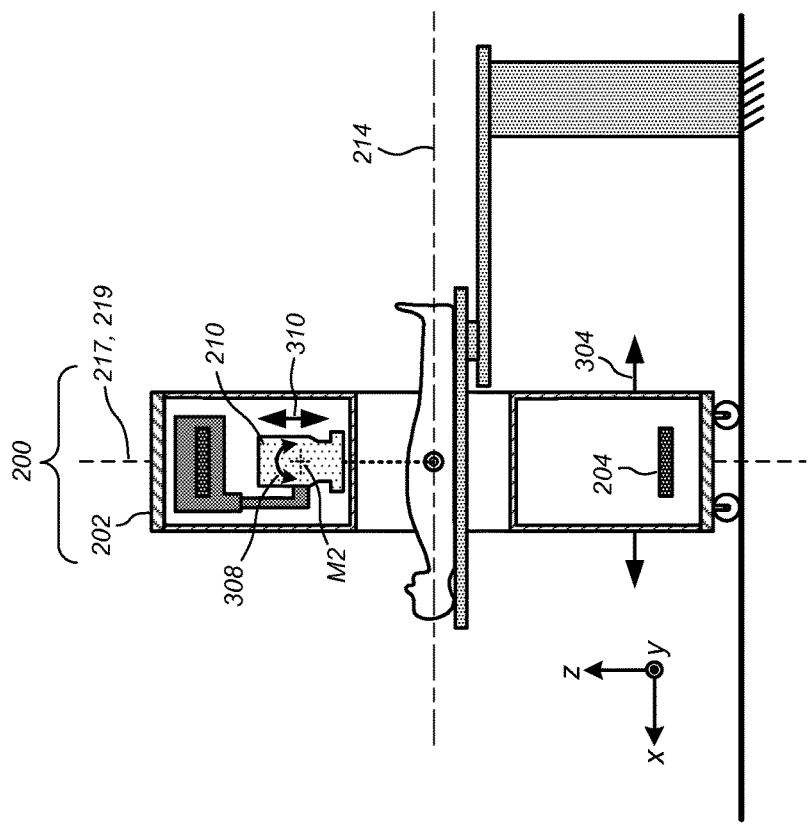

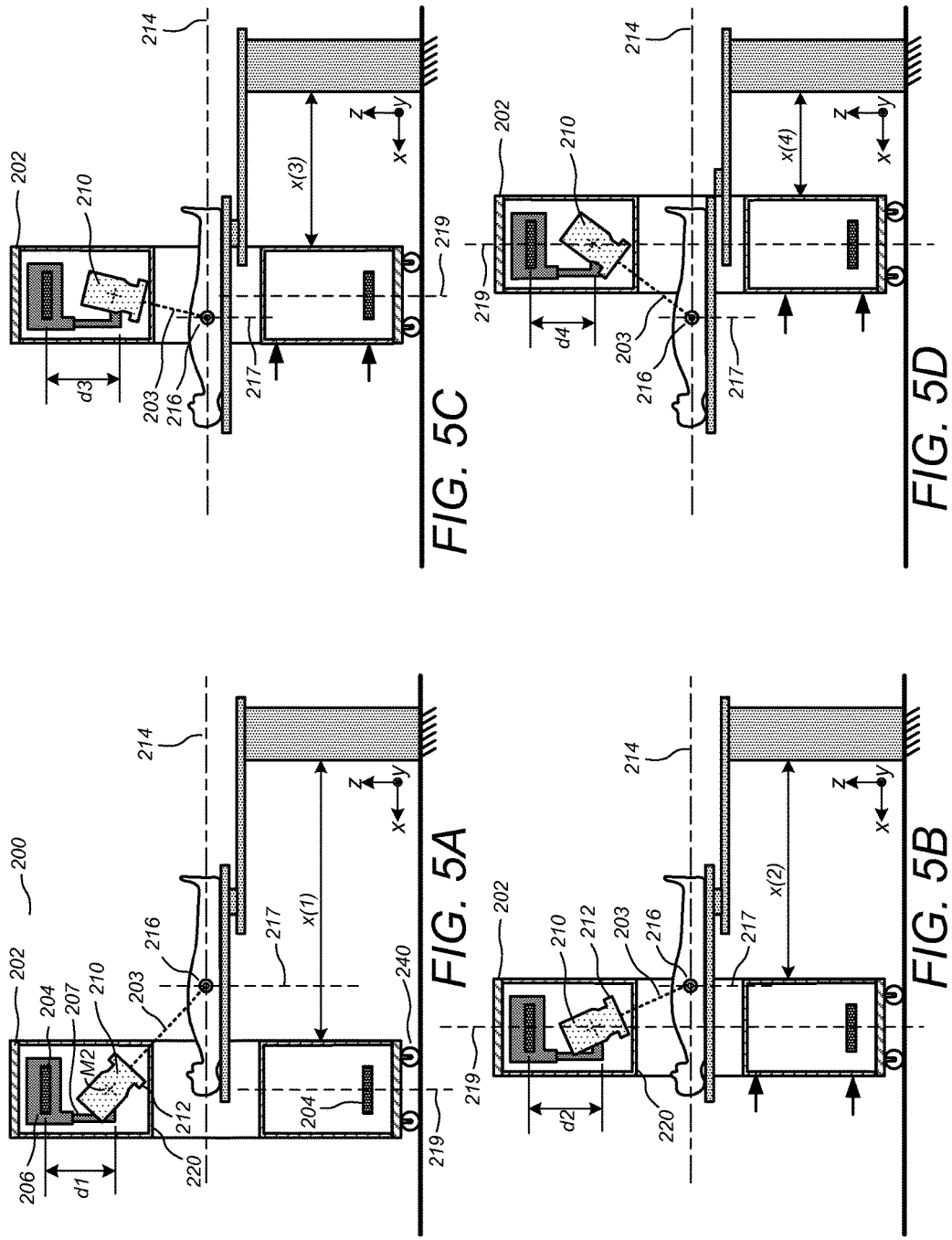

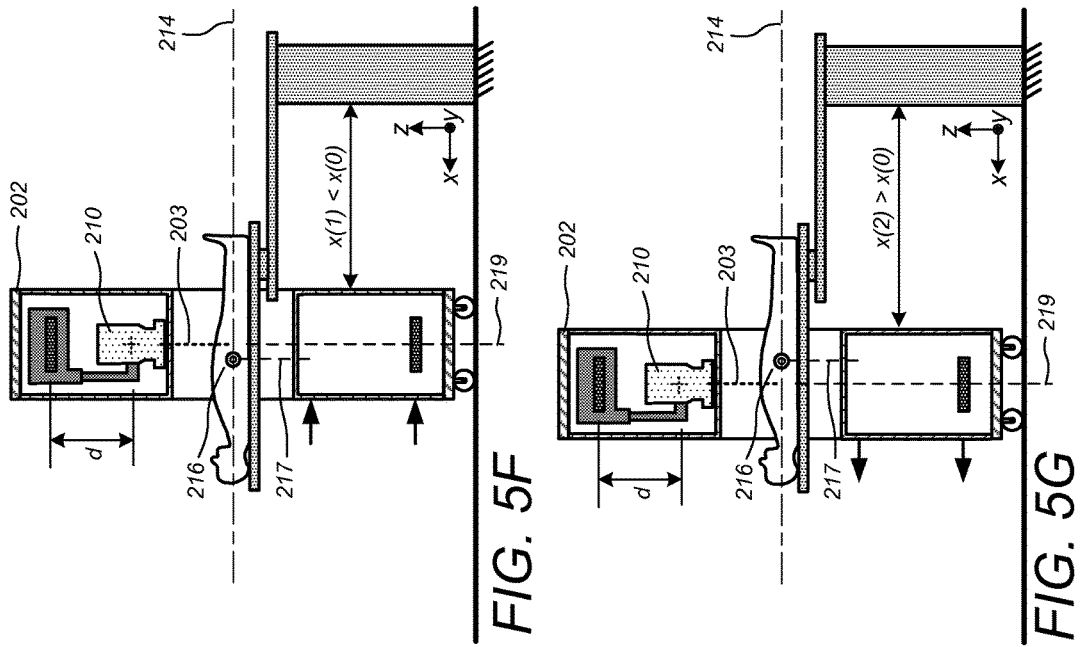

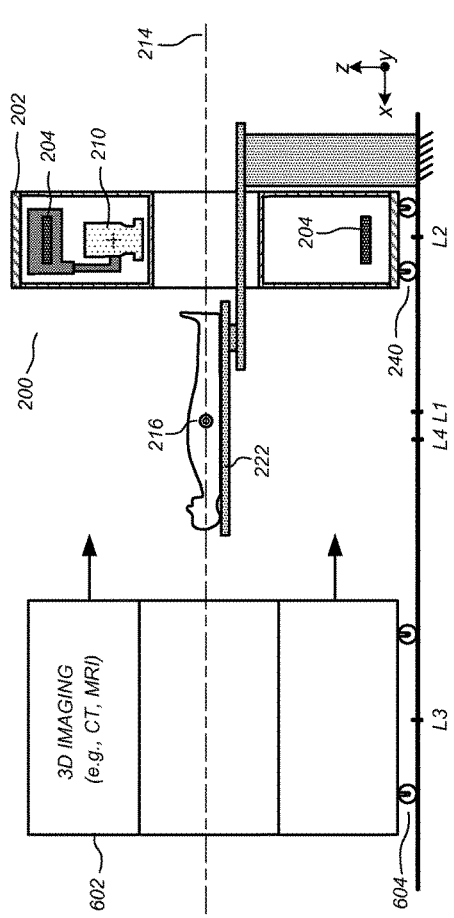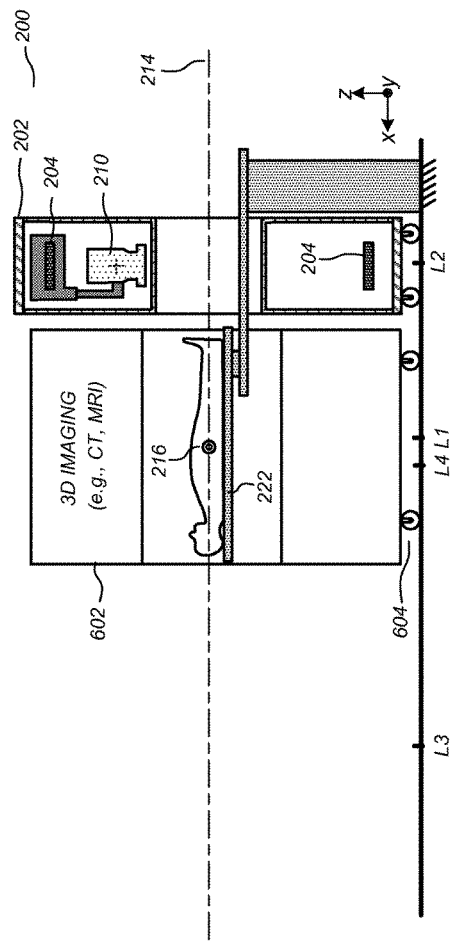
FIG. 6A
FIG. 6B

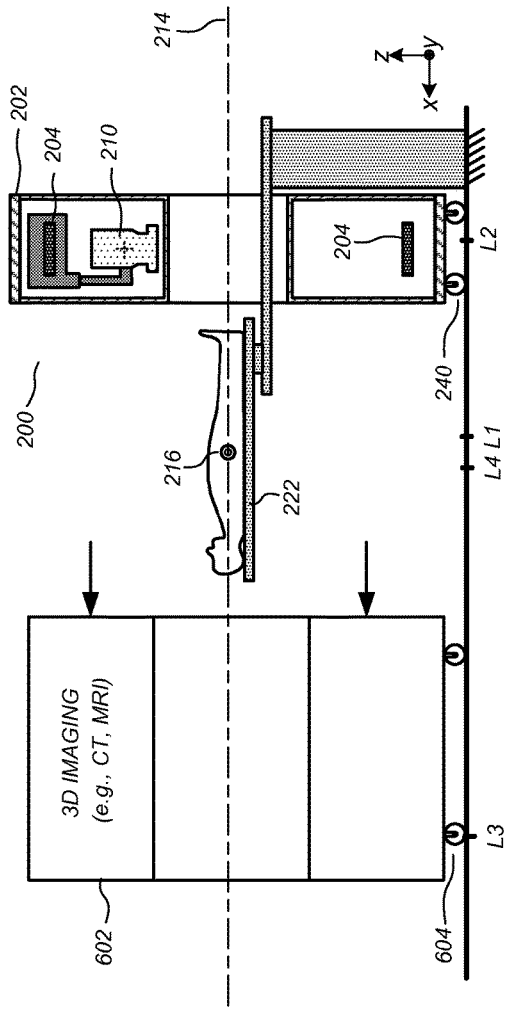
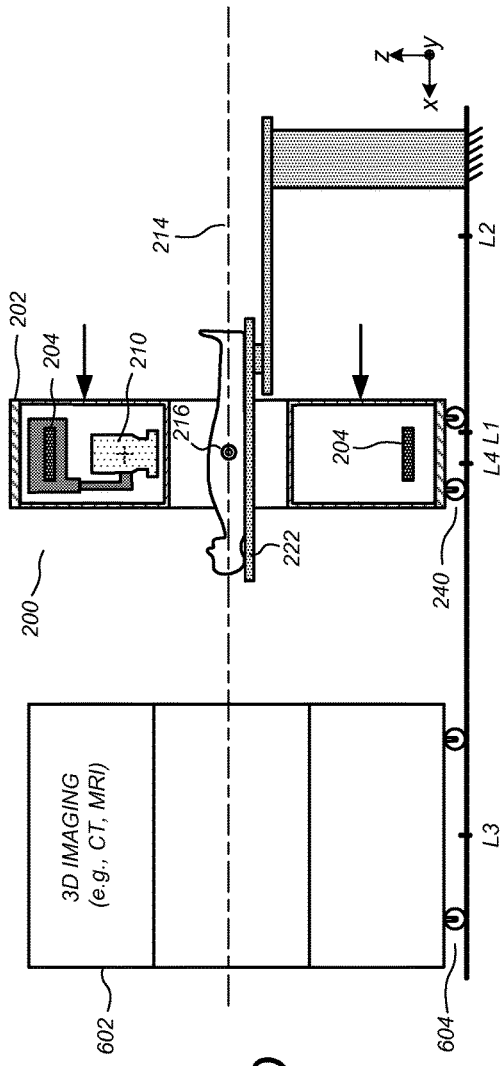

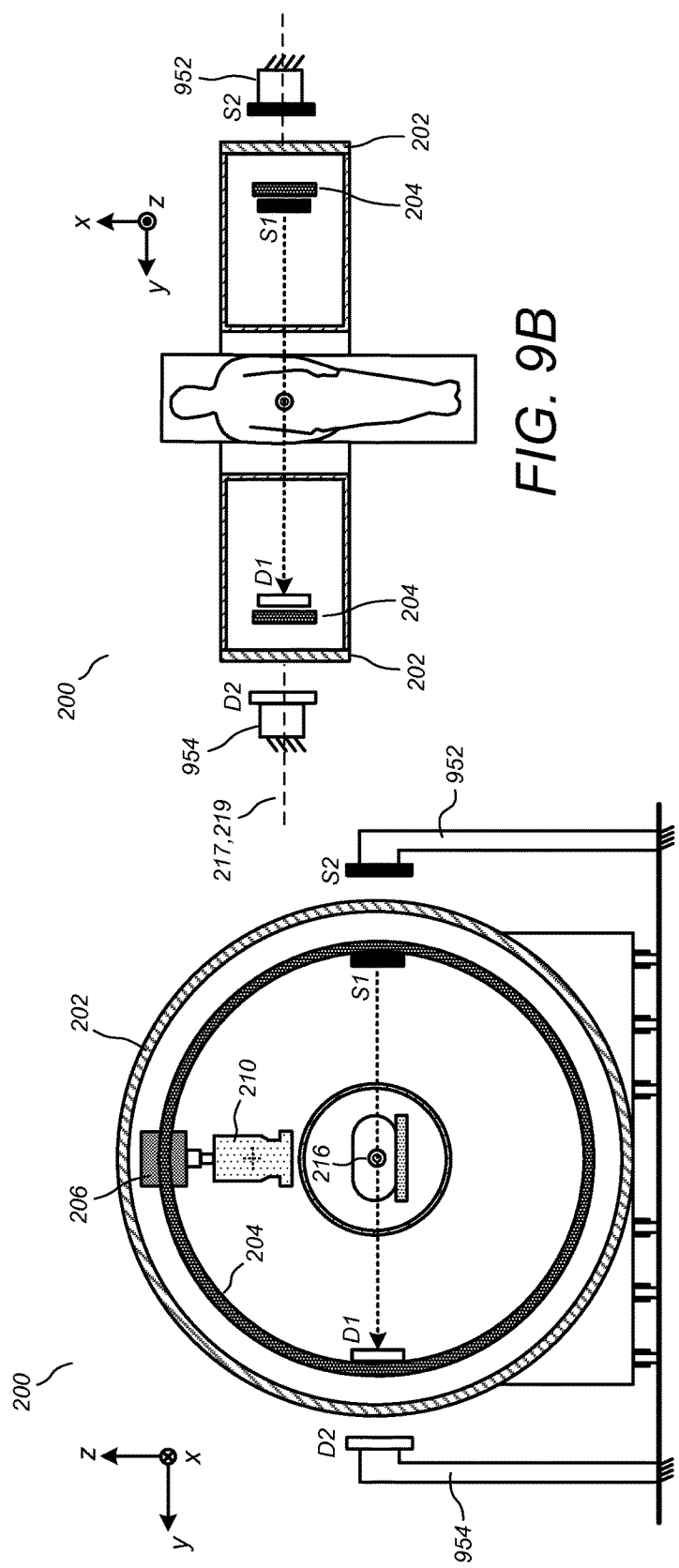

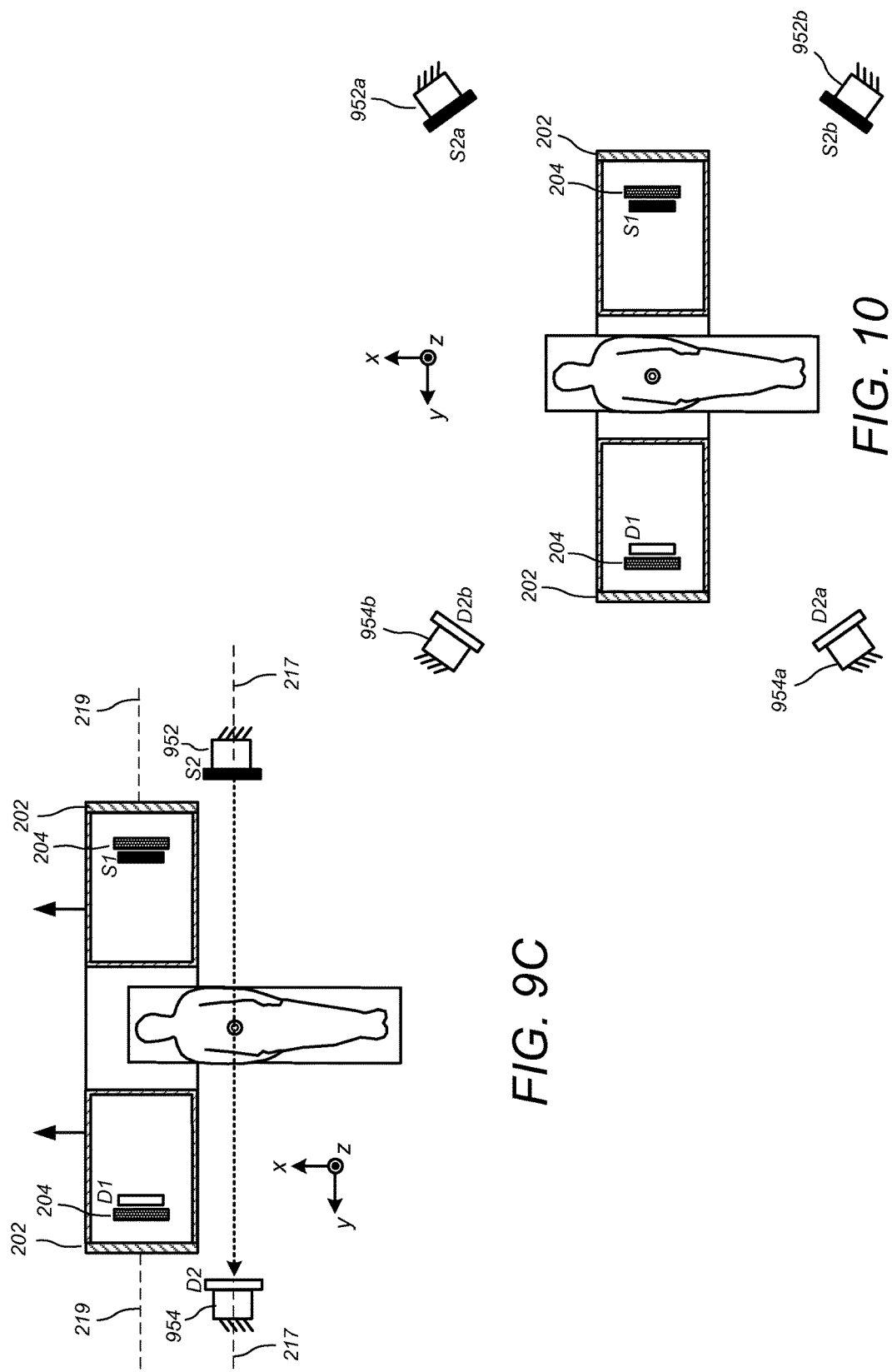

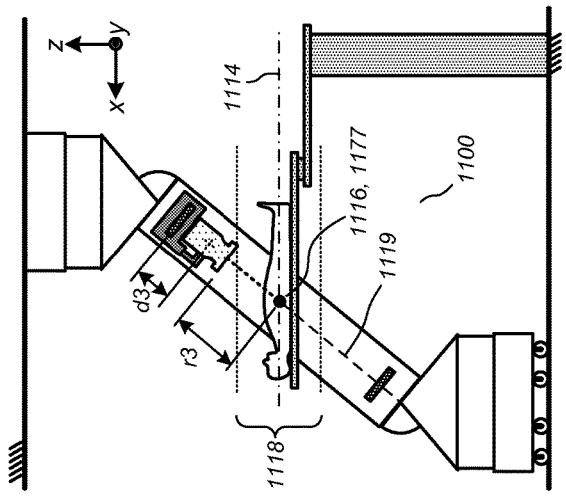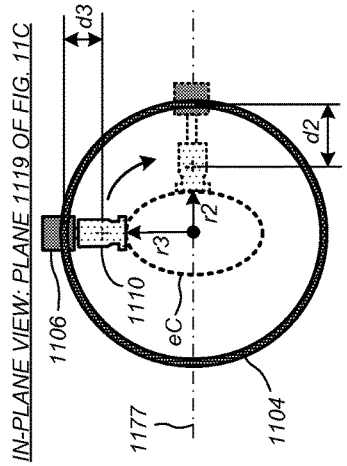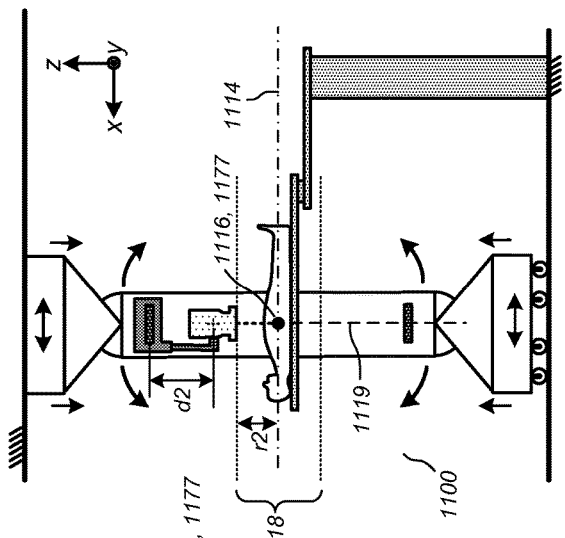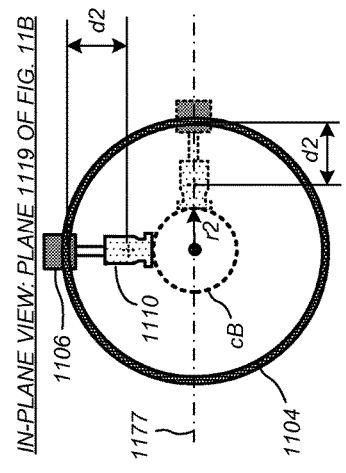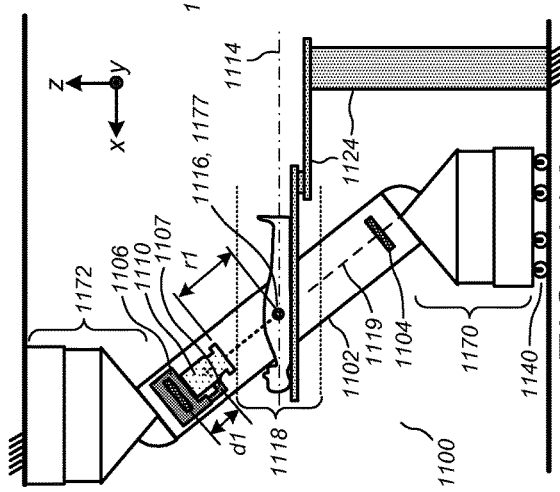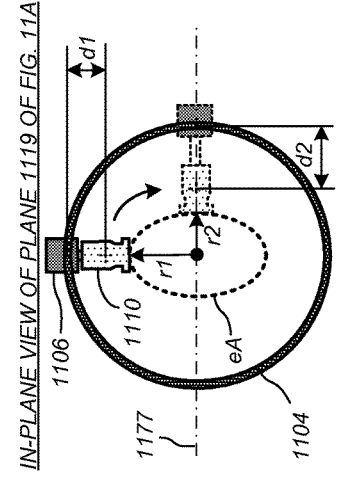

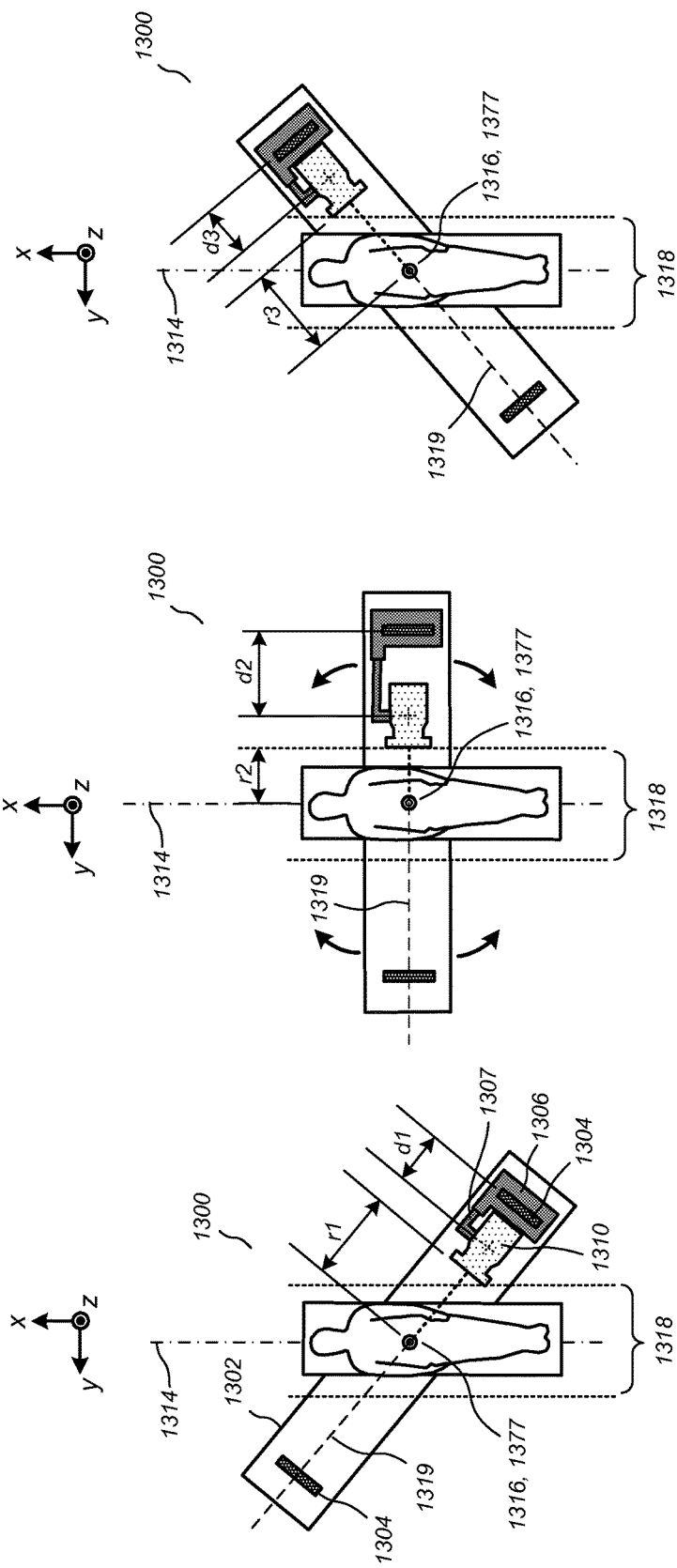

RADIATION TREATMENT DELIVERY
SYSTEM WITH TRANSLATABLE RING
GANTRY

CROSS-REFERENCE TO RELATED
APPLICATIONS

This application claims the benefit of U.S. Provisional Ser. No. 61/434,824 filed Jan. 20, 2011, which is incorporated by reference herein. The subject matter of this patent specification relates to the subject matter of the following commonly assigned applications: U.S. Ser. No. 13/033,571 filed Feb. 23, 2011; U.S. Ser. No. 13/033,584 filed Feb. 23, 2011; International Application No. PCT/US11/25936 filed Feb. 23, 2011; U.S. Prov. Ser. No. 61/352,637 filed Jun. 8, 2010; U.S. Prov. Ser. No. 61/371,732 filed Aug. 8, 2010; and U.S. Prov. Ser. No. 61/371,733 filed Aug. 8, 2010. The subject matter of this patent specification also relates to the subject matter of the commonly assigned U.S. Ser. No. 13/088,321, entitled "Ring Gantry Radiation Treatment Delivery System With Dynamically Controllable Inward Extension Of Treatment Head," filed Apr. 15, 2011, which is being filed on the same day as the instant patent application. Each of the above-referenced patent applications are incorporated by reference herein.

FIELD

This patent specification relates to the use of radiation for medical treatment purposes. More particularly, this patent specification relates to radiation treatment systems.

BACKGROUND

Pathological anatomies such as tumors and lesions can be treated with an invasive procedure, such as surgery, which can be harmful and full of risks for the patient. A non-invasive method to treat a pathological anatomy (e.g., tumor, lesion, vascular malformation, nerve disorder, etc.) is external beam radiation therapy, which typically uses a therapeutic radiation source, such as a linear accelerator (LINAC), to generate radiation beams, such as x-rays. In one type of external beam radiation therapy, a therapeutic radiation source directs a sequence of x-ray beams at a tumor site from multiple co-planar angles, with the patient positioned so the tumor is at the center of rotation (isocenter) of the beam. As the angle of the therapeutic radiation source changes, every beam passes through the tumor site, but passes through a different area of healthy tissue on its way to and from the tumor. As a result, the cumulative radiation dose at the tumor is high and that to healthy tissue is relatively low.

The term "radiosurgery" refers to a procedure in which radiation is applied to a target region at doses sufficient to necrotize a pathology in fewer treatment sessions or fractions than with delivery of lower doses per fraction in a larger number of fractions. Radiosurgery is typically characterized, as distinguished from radiotherapy, by relatively high radiation doses per fraction (e.g., 500-2000 centiGray), extended treatment times per fraction (e.g., 30-60 minutes per treatment), and hypo-fractionation (e.g., one to five fractions or treatment days). Radiotherapy is typically characterized by a low dose per fraction (e.g., 100-200 centiGray), shorter fraction times (e.g., 10 to 30 minutes per treatment) and hyper-fractionation (e.g., 30 to 45 fractions). For convenience, the term "radiation treatment" is used herein to mean radiosurgery and/or radiotherapy unless otherwise noted.

Image-guided radiation therapy (IGRT) systems include gantry-based systems and robotic arm-based systems. In gantry-based systems, a gantry rotates the therapeutic radiation source around an axis passing through the isocenter. Gantry-based systems include C-arm gantries, in which the therapeutic radiation source is mounted, in a cantilever-like manner, over and rotates about the axis passing through the isocenter. Gantry-based systems further include ring gantries having generally toroidal shapes in which the patient's body extends through a bore of the ring/toroid, and the therapeutic radiation source is mounted on the perimeter of the ring and rotates about the axis passing through the isocenter. Traditional gantry systems (ring or C-arm) deliver therapeutic radiation in single plane (i.e., co-planar) defined by the rotational trajectory of the radiation source. Examples of C-arm systems are manufactured by Siemens of Germany and Varian Medical Systems of California. In robotic arm-based systems, the therapeutic radiation source is mounted on an articulated robotic arm that extends over and around the patient, the robotic arm being configured to provide at least five degrees of freedom. Robotic arm-based systems provide the capability to deliver therapeutic radiation from multiple out-of-plane directions, i.e., are capable of non-coplanar delivery. Accuray Incorporated of California manufactures a system with a radiation source mounted on a robotic arm for non-coplanar delivery of radiation beams.

Associated with each radiation therapy system is an imaging system to provide in-treatment images that are used to set up and, in some examples, guide the radiation delivery procedure and track in-treatment target motion. Portal imaging systems place a detector opposite the therapeutic source to image the patient for setup and in-treatment images, while other approaches utilize distinct, independent image radiation source(s) and detector(s) for the patient set-up and in-treatment images. Target or target volume tracking during treatment is accomplished by comparing in-treatment images to pre-treatment image information. Pre-treatment image information may comprise, for example, computed tomography (CT) data, cone-beam CT data, magnetic resonance imaging (MRI) data, positron emission tomography (PET) data or 3D rotational angiography (3DRA) data, and any information obtained from these imaging modalities (for example and without limitation digitally reconstructed radiographs or DRRs).

In one common scenario, the therapeutic source is a linear accelerator (LINAC) producing therapeutic radiation (which can be termed an "MV source") and the imaging system comprises one or more independent x-ray imaging sources producing relatively low intensity lower energy imaging radiation (each of which can be termed a "kV source"). In-treatment images can comprise one or more (preferably two) two-dimensional images (typically x-ray) acquired at one or more different points of view (e.g., stereoscopic x-ray images), and are compared with two-dimensional DRRs derived from the three dimensional pre-treatment image information. A DRR is a synthetic x-ray image generated by casting hypothetical x-rays through the 3D imaging data, where the direction and orientation of the hypothetical x-rays simulate the geometry of the in-treatment x-ray imaging system. The resulting DRR then has approximately the same scale and point of view as the in-treatment x-ray imaging system, and can be compared with the in-treatment x-ray images to determine the position and orientation of the target, which is then used to guide delivery of radiation to the target.

There are two general goals in radiation therapy: (i) to deliver a highly conformal dose distribution to the target volume; and (ii) to deliver treatment beams with high accuracy throughout every treatment fraction. A third goal is to accomplish the two general goals in as little time per fraction as possible. Delivering a more conformal dose distribution requires, for example, the ability to deliver non-coplanar beams. Delivering treatment beams accurately requires the ability to track the location of the target volume intrafraction. The ability to increase delivery speed requires the ability to accurately, precisely, and quickly move the radiation source without hitting other objects in the room or the patient, or violating regulatory agency speed limitations.

One or more issues arise with respect to known radiation therapy systems that are at least partially addressed by one or more of the preferred embodiments described further hereinbelow. Generally speaking, these issues are brought about by a tension in known radiation therapy systems between mechanical stability and system versatility, a tension that becomes more pronounced as the desired use of radiation therapy expands from head-only applications to applications throughout the body, such as (without limitation) the lungs, liver, and prostate. Robot arm-based systems tend to allow for larger ranges of radiation beam angles for different body parts than ring or C-arm gantry-based systems, especially when it is desired to keep the patient couch motionless during the radiation therapy session. Accordingly, robot arm-based systems generally tend to allow for more versatility in the kinds of therapy plans that may be available to the patient in comparison to C-arm and ring gantry-based systems. Further in view of the very heavy nature of most therapeutic radiations sources, which can weigh hundreds of kilograms, systems based on mounting of the therapeutic radiation source on a C-arm gantry suffer from undesired in-treatment deformation of the mount structures, which deformation is difficult to model or predict and leads to beam delivery errors and/or increased therapy planning margins due to the inability to precisely and accurately identify where the beam is pointed in three-dimensional space.

Ring gantry-based systems, on the other hand, tend to exhibit relatively high mechanical stability, i.e., less of the deformation problems exhibited by C-arm gantry-based systems, and thus can reproducibly and accurately position the radiation source, including doing so at relatively high mechanical drive speeds. However, as discussed above, gantry-based systems (like C-arm systems) tend to provide a lesser range of achievable angles for the introduction of therapeutic radiation into different body parts and, therefore, provide a narrower array of radiation treatment options as compared to robot arm-based systems.

X-ray tomosynthesis refers to the process of acquiring a number of two-dimensional x-ray projection images of a target volume using x-rays that are incident upon the target volume at a respective number of different angles, followed by the mathematical processing of the two-dimensional x-ray projection images to yield a set of one or more tomosynthesis reconstructed images representative of one or more respective slices of the target volume, wherein the number of x-ray projection images is less than that in a set that would be required for CT image reconstruction, and/or the number or range of incident radiation angles is less than would be used in a CT imaging procedure. Commonly, a plurality of tomosynthesis reconstructed images are generated, each being representative of a different slice of the target volume, and therefore a set of tomosynthesis reconstructed images is sometimes referred to as a tomosynthesis volume. As used herein, the term tomosynthesis projection image refers to one of the two-dimensional x-ray projection images acquired during the tomosynthesis imaging process.

For purposes of the above terminology, for some preferred embodiments, a set of images that is required for CT image reconstruction is considered to include images (e.g., 300 or more) generated over a range of incident angles that is 180 degrees plus the fan beam angle. For some preferred embodiments, the x-ray projection images for constructing a tomosynthesis image are taken over an angular range between 1 degree and an angular range value that is less than that needed for a complete projection set for CT imaging (e.g., 180 degrees plus the fan angle), wherein the number of projection images generated in this range is a value that is between 2 and 1000. In other preferred embodiments, the x-ray projection images for constructing a tomosynthesis image are taken over an angular range of between 5 degrees and 45 degrees, wherein the number of projection images generated in this range is between 5 and 100.

X-ray tomosynthesis has been proposed as an in-treatment kV imaging modality for use in conjunction with radiation treatment systems. In U.S. Pat. No. 7,532,705B2 it is proposed to process the three-dimensional pre-treatment image information (e.g., a planning CT image volume) to generate digital tomosynthesis (DTS) reference image data of a target located within or on a patient, such as by simulating x-ray cone-beam projections through the planning CT image volume. Subsequently, with the patient on the treatment bed, DTS verification images are generated by acquiring a number of x-ray cone beam images at different angles. Target localization is then performed by comparing landmarks, such as bony structures, soft-tissue anatomy, implanted targets, and skin contours in the DTS reference image data and DTS verification image data. In U.S. Pat. No. 7,711,087B2 it is proposed to acquire tomosynthesis image data during a treatment session. For purposes of movement tracking during the treatment session, tomosynthesis reconstructed slices are processed directly in conjunction with reference CT data in a process that searches for a tomosynthesis reconstructed image that best matches a selected reference CT slice. The identity of the particular tomosynthesis reconstructed image that yields a maximum degree of match, together with the amount of spatial offset required for that tomosynthesis reconstructed image to achieve the peak match, is used to localize the target in three-dimensional space. The commonly assigned U.S. Pat. No. 6,778,850, which is incorporated by reference herein, also discloses the use of x-ray tomosynthesis images (more particularly, the use of relatively low clarity intra-treatment 3D images of the target region synthesized from a plurality of 2D diagnostic images acquired at different angles) of as an in-treatment kV imaging modality.

Cone beam CT (CBCT) has also been proposed as an in-treatment imaging modality for use in conjunction with radiation treatment systems, in some cases as a kV imaging modality and in other cases as an MV (portal) imaging modality. Whereas conventional CT imaging reconstructs 2D slices from 1D projections through a target volume, the 2D slices then being stacked to form a 3D volumetric image, CBCT imaging directly constructs a 3D volumetric image from 2D projections of the target volume. As known in the art, CBCT offers the ability to form a 3D image volume from a single gantry rotation (more specifically, a rotation of at least 180 degrees plus a fan beam angle) about the target volume, whereas conventional CT requires one rotation per slice (for single-row detectors) or 1/M rotations per slice (for newer quasi-linear multi-row detectors having M rows). CBCT also provides for a more isotropic spatial resolution, whereas conventional CT limits the spatial resolution in the longitudinal direction to the slice thickness. However, because conventional CT systems usually offer a substantially higher degree of collimation near their linear or quasi-linear row detectors than can usually be afforded by CBCT systems near their two-dimensional detectors, scattering noise and artifacts are more of a problem for CBCT systems than for conventional CT systems.

In U.S. Pat. No. 7,471,765B2 it is proposed to use a CBCT imaging system including a kV x-ray tube and a flat-panel imaging detector mounted on a LINAC gantry such that the kV radiation is approximately orthogonal to the MV treatment radiation from the LINAC. Prior to treatment, a CBCT planning image is acquired for treatment planning. Subsequently, before each treatment fraction, a CBCT image is acquired and compared to the CBCT pre-treatment planning image, and the results of the comparison are used to modify the treatment plan for that treatment fraction to compensate for interfraction setup errors and/or interfraction organ motion. Due to limitations in permissible gantry rotation speeds (e.g., one rotation per minute) which cause the CBCT acquisition time to be slow compared to breathing (or other physiological cycles) of the patient, a gating scheme synchronized to patient breathing (or other physiological cycles) is used during CBCT acquisition to reduce the deleterious effects of organ motion in the reconstructed images. Also due to the relatively slow CBCT acquisition time, the CBCT volume data is generally useful only for patient set-up before each treatment fraction, and not for intra-fraction motion correction.

X-ray source arrays such as field emission "cold cathode" x-ray source arrays represent a promising advance in medical imaging and offer potential advantages over conventional x-ray tube sources in several respects. A conventional x-ray tube usually comprises a tungsten, tantalum or rhenium cathode that is heated to approximately 2000° C. to cause electrons to be emitted thermionically, the free electrons then being accelerated toward an anode by a high electrical potential such as 120 kV. X-ray radiation usable for imaging is created when the thermionically generated electrons strike an anode, usually made of tungsten, molybdenum, or copper, at a focal spot of the x-ray tube, the collision causing the emission of x-ray photons. While historically being the only practical and cost-effective way to provide imaging x-ray radiation in medical imaging environments, conventional x-ray tube sources can bring about many design compromises in view of their relatively large size and weight, high operating temperatures, high power consumption, relatively modest temporal resolution (e.g., on/off switching times), and their minimal amenability to miniaturization or formation into closely spaced arrays.

As an alternative to conventional x-ray tube technology in which free electrons are generated by thermionic emission, alternative technologies have been introduced in which the free electrons are generated by field emission. In a field emission source, free electrons are emitted upon the application of a voltage to a material having a high emission density, such as certain carbon nanotube (CNT) materials. Because field emission of electrons is produced by a high electric field, no heating is necessary. Field emission sources are thus often referred to as cold cathode sources. Advantageously, the electron beams emitted by such materials may have low divergence and thus provide ease of focusing onto a focal spot. Moreover, the virtually instantaneous response of the source offers time gating capabilities that may even be on the order of nanoseconds. Because they can be made exceedingly small, field emission x-ray sources are highly amenable to formation into arrays. According to U.S. Pat. No. 7,505,562B2, which is incorporated by reference herein, devices having 1000 pixels per meter (i.e., 1000 individual x-ray sources per meter) with pulse repetition rates on the order of 10 MHz can be envisioned using technology within the current state of the art.

As used herein, the term x-ray source array refers to a source of x-rays comprising a plurality of spatially distinct, electronically activatible x-ray emitters or emission spots (focal spots) that are addressable on at least one of an individual and groupwise basis. Although most x-ray source arrays suitable for use with one or more of the preferred embodiments will commonly be of the field emission "cold cathode" type, the scope of the present teachings is not so limited. By way of example, other types of x-ray source arrays that may be suitable for use with one or more of the preferred embodiments include scanning-beam array X-ray sources in which an electron beam digitally scans across a tungsten transmission target thirty times per second, sequentially producing ten thousand individually collimated X-ray beams, as reported by Triple Ring Technologies, Inc., of Newark, Calif.

X-ray source arrays have been proposed for use in kV imaging systems associated with radiation treatment systems, such as in US20090296886A1. However, it is believed that substantial advances in the configuration, operation, and/or manner of integration of x-ray source arrays into IGRT systems, such as those provided by one or more of the preferred embodiments herein, are needed in order to achieve clinical practicality, effectiveness, and market acceptance. It is to be appreciated that although particularly advantageous in the context of IGRT systems, one or more of the preferred embodiments is also applicable to a wide variety of other medical imaging applications outside the realm of image-guided radiation treatment.

More generally, one or more issues arises with respect to known medical imaging and/or radiation treatment systems that is at least partially addressed by one or more of the preferred embodiments described further hereinbelow. For example, one issue that affects patient comfort is whether the physical configuration of the IGRT system provides a "tunnel-like" sensation for the patient, which can bring about unwanted feelings of claustrophobia, or whether it provides a more "open air" sensation for the patient. As another example, it would be desirable to provide an IGRT system in which it is not required to move the patient between the times of (i) the pretreatment and/or setup imaging process, and (ii) the treatment delivery process including in-treatment imaging, not only for promoting convenience and patient comfort, but also for increasing the precision of spatial registrations between the respective image sets to allow more precise radiation treatment delivery.

As yet another example, there is proposed in U.S. Pat. No. 7,188,999B2, which is incorporated by reference herein, a radiation treatment apparatus in which a LINAC is supported by an arc-shaped guide rail and circumferentially movable therealong, the arc-shaped guide rail being tiltable relative to a longitudinal axis along which the patient is positioned. By actuated tilting of the arc-shaped guide rail and actuated translation of the LINAC circumferentially along the arc-shaped guide rail, the LINAC may thereby be positioned, at least theoretically, substantially anywhere along an imaginary half-sphere centered at the isocenter. At least one difficulty arises, however, in that the LINAC could potentially collide or nearly collide with the skin surface of the patient when the arc-shaped guide rail is tilted off-normal relative to the longitudinal axis. Although U.S. Pat. No.

7,188,999B2 discusses one proposal that could at least partially address this problem, such proposal being to actuably elevate the entire gantry structure, including the entire arc-shaped guide rail, to different elevations above the floor of the treatment room, such proposal is believed to bring about one or more adverse consequences that are avoided by one or more of the preferred embodiments described further hereinbelow, and/or to suffer from one or more disadvantages not suffered by one or more of the preferred embodiments described further hereinbelow. Other issues arise as would be apparent to a person skilled in the art in view of the present teachings.

SUMMARY

Provided according to one preferred embodiment is a radiation treatment apparatus comprising a ring gantry having a central opening and a radiation treatment head coupled to the ring gantry. The radiation treatment head is rotatable around the central opening in at least a 180 degree arc. The radiation treatment apparatus further comprises a gantry translation mechanism configured to translate the ring gantry in a direction of a longitudinal axis extending through the central opening.

Also provided is a method for image guided radiation treatment (IGRT) of a body part of a patient, comprising positioning the patient along a longitudinal axis of an IGRT apparatus having a ring gantry with a central opening, the longitudinal axis extending through that central opening, the IGRT apparatus further comprising a radiation treatment head coupled to the ring gantry and rotatable around the central opening in at least a 180 degree arc, the IGRT apparatus further comprising a gantry translation mechanism configured to translate the ring gantry in a direction of the longitudinal axis. The IGRT apparatus is operated to apply non-coplanar radiation treatment to the body part during a treatment fraction, wherein the radiation treatment head is rotated around the central opening to a plurality of different gantry angles, and wherein the ring gantry is translated to a plurality of different longitudinal positions along the longitudinal axis.

Also provided is a radiation treatment apparatus comprising a ring gantry having a central opening sufficiently large to accommodate a body of a patient positioned along a longitudinal axis and extending therethrough, and further comprising a gantry tilting mechanism configured to tilt the ring gantry to a plurality of different tilt angles relative to the longitudinal axis. The apparatus further comprises a radiation treatment head coupled to the ring gantry and rotatable around the central opening in at least a 180 degree arc. The radiation treatment head is mechanically coupled to the ring gantry such that a distance by which the radiation treatment head extends inwardly toward the central opening relative to the ring gantry is dynamically controllable.

Also provided is a method for image guided radiation treatment of a body part of a patient, comprising positioning the patient along a longitudinal axis of an IGRT apparatus, the IGRT apparatus comprising a ring gantry having a central opening sufficiently large to accommodate the body of the patient and a gantry tilting mechanism configured to tilt the ring gantry to a plurality of different tilt angles relative to the longitudinal axis. A radiation treatment head is coupled to the ring gantry and is rotatable around the central opening in at least a 180 degree arc, and is mechanically coupled to the ring gantry such that a distance by which the radiation treatment head extends inwardly toward the central opening relative to the ring gantry is dynamically controllable. The IGRT apparatus is operated to apply non-coplanar radiation treatment to the body part during a treatment fraction, the operating comprising rotating the radiation treatment head around the central opening to a plurality of different gantry angles, the operating further comprising tilting the ring gantry to the plurality of different tilt angles relative to the longitudinal axis.

Also provided is a radiation treatment apparatus comprising a ring gantry having a central opening sufficiently large to accommodate a body of a patient positioned along a longitudinal axis and extending therethrough. The apparatus further comprises a radiation treatment head coupled to the ring gantry and rotatable around the central opening in at least a 180 degree arc. The radiation treatment head is mechanically coupled to the ring gantry such that a distance by which the radiation treatment head extends inwardly toward the central opening relative to the ring gantry is dynamically controllable.

Also provided is a method for image guided radiation treatment of a body part of a patient, comprising positioning the patient along a longitudinal axis of an IGRT apparatus, the IGRT apparatus comprising a ring gantry having a central opening sufficiently large to accommodate the body of the patient. A radiation treatment head is coupled to the ring gantry and is rotatable around the central opening in at least a 180 degree arc, and is mechanically coupled to the ring gantry such that a distance by which the radiation treatment head extends inwardly toward the central opening relative to the ring gantry is dynamically controllable. The IGRT apparatus is operated to apply non-coplanar radiation treatment to the body part during a treatment fraction, the operating comprising rotating the radiation treatment head around the central opening to a plurality of different gantry angles, the operating further comprising dynamically controlling the distance by which the radiation treatment head extends inwardly through the plurality of gantry angles.

BRIEF DESCRIPTION OF THE DRAWINGS

FIGS. 2A-2B illustrate side and axial cut-away views, respectively, of an image-guided radiation treatment (IGRT) apparatus according to a preferred embodiment;

FIGS. 3A-3B illustrate side and axial cut-away views, respectively, of an IGRT apparatus according to a preferred embodiment;

FIGS. 5A-5D illustrate side cut-away views of the IGRT apparatus of FIG. 3 for a plurality of different longitudinal positions of a ring gantry thereof during conical non-coplanar or cono-helical non-coplanar radiation treatment delivery;

FIGS. 5E-5G illustrate side cut-away views of the IGRT apparatus of FIG. 3 for a plurality of different longitudinal positions of the ring gantry during helical non-coplanar radiation treatment delivery;

FIGS. 6A-6D illustrate longitudinal translation of a 3D imaging device and a ring gantry structure of an IGRT system according to a preferred embodiment for providing pretreatment and/or setup imaging in conjunction with radiation treatment delivery while allowing the patient to remain stationary;

FIGS. 9A-9C illustrate one axial and two top cut-away views, respectively, of an IGRT apparatus according to a preferred embodiment;

FIG. 10 illustrates a top cut-away view of an IGRT apparatus according to a preferred embodiment;

FIGS. 11A-11C illustrate side cut-away views of an IGRT apparatus including a ring gantry tilted around a horizontal tilt axis at different respective tilt angles according to a preferred embodiment;

FIGS. 12A-12C illustrate in-plane ring gantry cut-away views of the IGRT apparatus of FIGS. 11A-11C for the respective ring gantry tilt angles thereof, each including views of a radiation head thereof at two different gantry angles for illustrating dynamic inward/outward position control of the radiation head according to a preferred embodiment;

FIGS. 13A-13C illustrate top cut-away views of an IGRT apparatus including a ring gantry tilted around a vertical tilt axis at different respective tilt angles according to a preferred embodiment;

DETAILED DESCRIPTION

Figure 1:
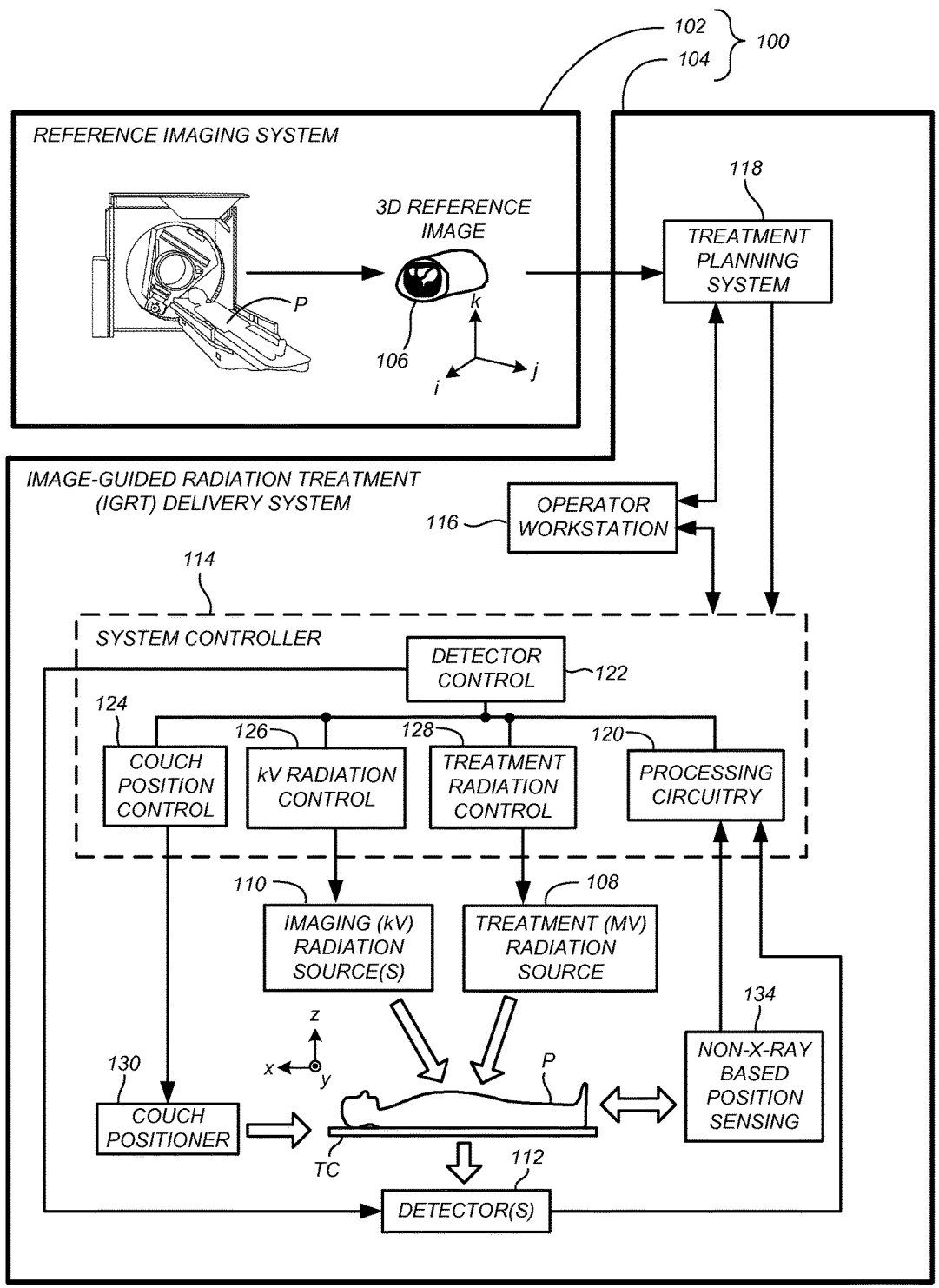
FIG. 1 illustrates a radiation treatment environment according to a preferred embodiment.

Described further hereinbelow are systems, methods, and related computer program products for image-guided radiation treatment (IGRT), including an image-guided radiation therapy (IGRT) system that provides an advantageous combination of high mechanical stability, versatility in radiation delivery, an open-air configuration, and an ability to keep the patient stationary between the times of (i) pretreatment and/or setup imaging, and (ii) treatment delivery including in-treatment imaging. In one preferred embodiment, a radiation treatment apparatus is provided, comprising a ring gantry having a central opening, a radiation treatment head coupled to the ring gantry and rotatable around the central opening in at least a 180 degree arc, and a gantry translation mechanism configured to translate the ring gantry in a direction of a longitudinal axis extending through the central opening. In one preferred embodiment, the ring gantry is housed within a ring gantry structure that has an overall length of less than about one meter along the longitudinal axis, which advantageously promotes a non-claustrophobic, "open-air" feel and experience for the patient.

In one preferred embodiment, the radiation treatment head is rotatable around the central opening in a full 360 degree arc.

In one preferred embodiment, the ring gantry defines a central ring gantry plane along which a center of mass of the radiation treatment head is maintained, and the radiation treatment head is pivotably mounted to the ring gantry in a manner that allows treatment radiation to be directed out of plane relative to the ring gantry plane. More preferably, the radiation treatment head is mounted to allow further pivotable movement such that treatment radiation can be directed off-center relative to a central longitudinal axis passing through the isocenter. Advantageously, a rich variety of different treatment types and treatment profiles are made possible including, but not limited to, conical non-coplanar rotational arc therapy and cono-helical non-coplanar rotational arc therapy. According to another preferred embodiment, yet another degree of freedom is provided by mounting the radiation treatment head to the ring gantry such that a radial distance between the radiation treatment head and the central longitudinal axis is dynamically controllable.

For one preferred embodiment, in-treatment imaging is provided by a first kV imaging system including a first imaging source and a first imaging detector that are translatable with the ring gantry along the longitudinal axis. The first imaging source and first imaging detector can be mounted to the ring gantry to be rotatable in unison with the radiation treatment head around the central opening, or alternatively can be fixed to a frame of the ring gantry structure such that they are not rotatable around the central opening but are still translatable along the longitudinal axis with the ring gantry. Preferably, a second kV imaging system including a second imaging source and a second imaging detector are also provided, the second kV imaging system being either stationary along the longitudinal axis or independently translatable along the longitudinal axis relative to the ring gantry. The second kV imaging system is fixably positioned and/or movably controlled such that, when the ring gantry is moved longitudinally such that its central plane is removed from the isocenter, the second kV imaging system can "take over" for the first kV imaging system to provide the necessary in-treatment image information.

According to another preferred embodiment, the treatment vault is also outfitted with a 3D imaging device (e.g., CT, MRI) separate from the ring gantry structure containing the ring gantry and radiation treatment head, wherein the 3D imaging device is translatable along the central longitudinal axis separately and independently of the ring gantry structure. The ring gantry structure is translatable along the central longitudinal axis between a first location for which it longitudinally encompasses the isocenter and a second location away from the isocenter. Similarly, the 3D imaging device is translatable along the central longitudinal axis between a third location for which it is away from the isocenter and a fourth location for which it longitudinally encompasses the isocenter. Advantageously, this provides an ability to keep the patient completely stationary while achieving both (a) pre-treatment and/or setup imaging of the target tissue volume by the 3D imaging device, and (b) delivery of radiation treatment to the target tissue volume by the radiation treatment head. For pre-treatment and/or setup imaging, the ring gantry structure is moved out of the way while the 3D imaging device acquires the pre-treatment and/or setup images, while for delivery of radiation treatment the 3D imaging device is moved out of the way to allow the ring gantry-mounted radiation treatment head to perform radiation delivery, all without needing to translate, rotate, or otherwise move the patient.

Also provided according to one or more preferred embodiments is a radiation treatment apparatus comprising a ring gantry having a central opening sufficiently large to accommodate a body of a patient positioned along a fixed longitudinal axis and extending therethrough, and further comprising a gantry tilting mechanism configured to tilt the ring gantry to a plurality of different tilt angles relative to the longitudinal axis. The apparatus further comprises a radiation treatment head coupled to the ring gantry and rotatable around the central opening in at least a 180 degree arc, and more preferably a complete 360 degree arc. For one preferred embodiment, the ring gantry is tiltable without being longitudinally translatable in the treatment vault, while in another preferred embodiment the ring gantry is both tiltable and longitudinally translatable in the treatment vault. For one preferred embodiment, the ring gantry is tiltable around a horizontal tilt axis, while in another preferred embodiment the ring gantry is tiltable around a vertical tilt axis. For preferred embodiments in which the ring gantry is both tiltable and longitudinally translatable, the tilt axis will likewise be translatable along with the ring gantry. One or more kV imaging systems is provided, which can include one or more on-gantry kV imaging systems that are mounted to the ring gantry and that are therefore tiltable and/or translatable therewith. The one or more kV imaging systems can further and/or alternatively include one or more independently movable kV imaging systems that move in the treatment vault independently of the ring gantry, and can further and/or alternatively include one or more fixed kV imaging systems that are fixed relative to the treatment vault.

Provided in conjunction with the tiltable ring gantry according to a preferred embodiment is a mechanical coupling between the radiation treatment head and the ring gantry designed to facilitate and promote dynamic control of a distance by which the radiation treatment head extends inwardly toward the central opening relative to the ring gantry. By way of example, in one preferred embodiment the radiation treatment head is coupled to the ring gantry by a telescoping arm configured to dynamically extend, under computerized control, toward and away from a center of the ring gantry plane. In one preferred embodiment, the inward extension distance is dynamically controlled as the radiation treatment head is rotated through a plurality of gantry angles around the central opening, the dynamic control being applied in a manner such that the radiation treatment head is maintained adjacently outside a predefined cylindrical buffer zone extending around the patient along the longitudinal axis. For instances in which the ring gantry is tilted at a non-normal angle relative to the longitudinal axis, the tip of the radiation treatment head follows a generally elliptical trajectory, the telescoping arm being relatively retracted at locations for which the circumference of the ring gantry comes closer to the buffer zone, the telescoping arm being relatively extended at locations for which the circumference of the ring gantry is farther away from the buffer zone. For preferred embodiments in which the ring gantry is both tiltable and longitudinally translatable, the treatment vault can also outfitted with a separate 3D imaging device (e.g., CT, MRI) translatable along the longitudinal axis separately and independently of the ring gantry structure, for providing the ability to keep the patient completely stationary while achieving both (i) pre-treatment and/or setup imaging, and (ii) delivery of radiation treatment.

FIG. 1 illustrates a radiation treatment environment 100 within which one or more of the preferred embodiments is advantageously applied. The radiation treatment environment 100 includes a reference imaging system 102 and an IGRT system 104. Reference imaging system 102 usually comprises a high precision volumetric imaging system such as a computed tomography (CT) system or a nuclear magnetic resonance imaging (MRI) system. In view of cost and workflow considerations in many clinical environments, the reference imaging system 102 is often a general purpose tool used for a variety of different purposes in the clinic or hospital environment, and is not specifically dedicated to the IGRT system 104. Rather, the reference imaging system 102 is often located in its own separate room or vault and is purchased, installed, and/or maintained on a separate and more generalized basis than the IGRT system 104. Accordingly, for the example of FIG. 1, the reference imaging system 102 is illustrated as being distinct from the IGRT system 104. Notably, for other radiation treatment environments that are not outside the scope of the present teachings, the reference imaging system 102 can be considered as an integral component of the IGRT system 104.

IGRT system 104 comprises a radiation treatment (MV) source 108 that selectively applies high-energy x-ray treatment radiation to a target volume of a patient P positioned on a treatment couch TC. The MV source 108 applies the treatment radiation under the control of a system controller 114, and more particularly a treatment radiation control subsystem 128 thereof. System controller 114 further comprises processing circuitry 120, a detector controller 122, a couch position controller 124, and a kV radiation controller 126 each programmed and configured to achieve one or more of the functionalities described further herein. One or more imaging (kV) radiation sources 110 selectively emit relatively low-energy x-ray imaging radiation under the control of kV radiation controller 126, the imaging radiation being captured by one or more imaging detectors 112. In alternative preferred embodiments, one or more of the imaging detectors 112 can be a so-called portal imaging detector that captures high-energy x-ray treatment radiation from MV source 108 that has propagated through the target volume.

For one preferred embodiment, the kV imaging radiation sources 110 include both a two-dimensional stereotactic x-ray imaging system and a tomosynthesis imaging system. For other preferred embodiments, only a two-dimensional stereotactic x-ray imaging system is provided, while for still other preferred embodiments only a tomosynthesis imaging system is provided. Preferably, each of the stereotactic x-ray imaging system and the tomosynthesis imaging system are characterized by either (a) a fixed, predetermined, nonmoving geometry relative to the (x, y, z) coordinate system of the treatment room, or (b) a precisely measurable and/or precisely determinable geometry relative to the (x, y, z) coordinate system of the treatment room in the event they are dynamically moveable. The MV radiation source 108 should also, of course, have a precisely measurable and/or precisely determinable geometry relative to the (x, y, z) coordinate system of the treatment room.

A couch positioner 130 is actuated by the couch position controller 124 to position the couch TC. Optionally, a non-x-ray based position sensing system 134 senses position and/or movement of external marker(s) strategically affixed to the patient, and/or senses position and/or movement of the patient skin surface itself, using one or more methods that do not involve ionizing radiation, such as optically based or ultrasonically based methods. IGRT system 104 further includes an operator workstation 116 and a treatment planning system 118.

FIGS. 2A-2B illustrate an IGRT system according to one or more preferred embodiments including a translatable ring gantry structure 200. Ring gantry structure 200 comprises a frame 202 within which is disposed a ring gantry 204. Mounted to the ring gantry 204 is a radiation treatment head 210, such as and without limitation a linear accelerator (LINAC) or a compact proton source, which includes thereon an end collimator 212, such as a multi-leaf collimator (MLC), and which provides a therapeutic radiation beam 203. The radiation treatment head 210 is mounted to the ring gantry 204 by a mount 206 that includes an arm 207. For one preferred embodiment, the radiation treatment head 210 comprises a compact lightweight LINAC, such as an X-band or C-band LINAC in a compact configuration without a bending magnet. This allows a compact system design in which all moving components are behind a fixed surface covering (see shielding structure 220), thus eliminating the risk of collision with the patient and enabling higher rotation speeds (there is a U.S. regulatory standard that does not allow rotation speeds higher than one rotation per minute if there is a risk of collision with the patient). In an alternative embodiment, the compact accelerator can include a bending magnet.

The ring gantry 204 and radiation treatment head 210 are configured such that the radiation treatment head 210 is rotatable around a longitudinally oriented central axis 214 passing through an isocenter 216. Any of a variety of different mechanisms, as would be apparent to a person skilled in the art in view of the present disclosure, can be used to achieve such rotating functionality, including mechanisms in which the ring gantry 204 is fixed while the mount 206 slides or rolls therearound, mechanisms in while the entire ring gantry 204 rotates and the mount 206 is affixed to a single point thereon, and various combinations thereof. For cases in which the ring gantry 204 remains fixed while the mount 206 slides or rolls therearound, it would be readily appreciated that the term "gantry angle" may still be used to represent the angular disposition of the radiation treatment head relative to the central longitudinal axis as viewed axially from an end of the device, even though the ring gantry itself is not rotating and instead the radiation treatment head is being translated circumferentially therearound.

The skilled artisan will appreciate that any of a variety of different mechanical support schemes that allow such variation of the gantry angle can be used (e.g., anti-friction sleeves, slip bearings, roller bearings, etc.). For simplicity of disclosure, the descriptions hereinbelow are presented for the case in which the entire ring gantry 204 rotates and the mount 206 is affixed to a single point thereon, although it is to be appreciated that the scope of the present teachings is not so limited.

The ring gantry 204 and radiation treatment head 210 are configured and dimensioned so as to allow a central opening (central bore) 218 to exist, that is, an opening sufficient to allow a patient P to be positioned therethrough without the possibility of being incidentally contacted by the radiation treatment head 210 or other mechanical components as it rotates about patient P. Preferably, a shielding structure 220 is provided to line the boundary of the central bore 218 as well as to cover the sides of ring gantry structure 200. In addition to preventing unexpected movement of the patient's hands or other body part into collision with moving parts, the shielding structure 220 can reduce the sense of intimidation that the patient might feel in view of the large moving parts in the device. The shielding structure 220 provides the ability to maximize the rotation speed of the gantry, while still meeting all regulatory safety requirements. The shielding structure 220 should be formed of a material that is substantially transparent to the therapeutic and imaging radiation, and optionally can be visibly opaque as well. The central bore 218 could alternatively be termed a cylindrical buffer zone, or perhaps more colloquially a "no-fly zone," the alternative terminology being particularly appropriate for instances in which the shielding structure 220 is not included.

Associated with the IGRT system is an imaginary plane, termed herein a transverse isocentric plane 217, that is orthogonal to the rotation axis 214 and passes through the isocenter 216. Associated with the ring gantry structure 200 including ring gantry 204 is a ring gantry plane 219 which, while it may at certain times and/or for certain procedures remain coplanar with the transverse isocentric plane 217 as illustrated in FIG. 2A, can become separated in the longitudinal direction from the transverse isocentric plane 217 by a translation of the ring gantry structure 202 in the longitudinal direction. As used herein, an isocenter is a fixed physical point in a treatment room (treatment vault). A treatment center is a point within a target volume of the patient defined by a physician during treatment planning, normally based on a pretreatment image reference frame. For isocentric treatment the treatment center is aligned with the isocenter during a set up procedure. Notably, even as the ring gantry structure 200 is translated in the longitudinal direction, the isocenter 216 remains at a fixed point in the treatment vault, and it is the ring gantry plane 219 that varies in longitudinal position.

Illustrated in FIGS. 2A-2B is a translational actuation mechanism 240 for translating the ring gantry structure 200 in the longitudinal direction. While shown by way of simplified example in FIGS. 2A-2B as wheels that may be driven by a motor (not shown), the translational actuation mechanism 240 can take on a variety of different forms, as would be apparent to a person skilled in the art in view of the present disclosure, to achieve such translational functionality. It should also be appreciated that, while shown as being rollably disposed on a floor 226 of a treatment vault, the ring gantry structure 200 can alternatively, or in conjunction therewith, be translatably coupled to the ceiling and/or one or more side walls of the treatment vault.

The skilled artisan will appreciate that the frame 202 can be made substantially thicker or otherwise reinforced at various locations than is indicated schematically in FIGS. 2A-2B, in accordance with the particular materials being used and other design considerations, for ensuring such mechanical stability. A patient couch 222 is provided for supporting the patient P, the patient couch 222 preferably being coupled to an automated patient positioning system 224 capable of manipulating the patient with three or more degrees of freedom (e.g., three orthogonal translations, one parallel to the rotation axis 214, two orthogonal to rotation axis 214, plus optionally one or more rotations). The skilled artisan will appreciate that many couches can be used in accordance with embodiments of the present invention.

Advantageously, the ring gantry structure 200 provides a high degree of patient visibility into the surrounding room to provide a less claustrophobic experience. Optionally, or alternatively, shielding structure 220 could be a structural supporting cylinder or hub to which frame 202 is mechanically connected at approximately opposite ends of the supporting cylinder or hub. In such an embodiment the hub will provide additional or alternative structural support in addition to or in lieu of frame 202. In another embodiment the hub (whether or not made from radiolucent material) and/or the shielding structure 220 has a longitudinal slit along the central opening 218 parallel to rotation axis 214 to allow radiation to pass therethrough unimpeded, thereby reducing the possibility of the so-called skin effect or to maximize skin sparing. As will be appreciated, the shielding structure 220 could still line the structural cylinder and need not necessarily possess the slit, thereby fully closing off patient view and access to the rotating radiation source. The slit, if viewable by a patient, could be constructed so as to minimize potential access to the rotating radiation source, and the patient would likely only see the rotating radiation source when it is at or near the top of the ring pointing approximately vertically down. As will be appreciated, the hub will rotate in approximate unison with the radiation head. Stated in a different way, as an additional option, the shielding structure 220 can be coupled such that it rotates with the ring gantry 204. Optionally, to maintain moving components behind a fixed surface covering as much as possible in view of skin sparing issues, a removable cover can be provided to "plug" the slit, which would be fitted for rotational therapy treatment. For treatments using just a few (1-4) static beams, where build up is most critical but rotation speed between beams is not, then the slit is kept open. For rotational arc therapy treatments where build up is not critical (because skin dose is smeared out over so many beam directions) but rotation speed is critical, then the plug is fitted into the slit. This can be achieved manually in pre-treatment with a totally removable plug, or alternatively there is provided a mechanically sliding system on the shielding structure 220 that can cover and uncover the slit under control and/or actuation of the treatment technician.

As illustrated in FIGS. 2A-2B, the radiation treatment head 210 is preferably coupled to the arm 207 of the mount 206 in a manner that allows pivoting of the radiation treatment head 210 around a first pivot axis M1, termed herein a primary pivot axis, and (iii) pivoting of the therapeutic radiation head 210 around a second axis M2, termed herein a secondary pivot axis, located at a right angle to M1. Preferably, the axes M1 and M2 each pass through the center of mass (CoM) of the therapeutic radiation head 210 (which is also coincident with the radiation source, e.g., the focal spot in a LINAC), the center of mass lies along the axis of the therapeutic radiation beam 203, and the center of mass is coincident with the ring gantry plane 219. Collectively, the primary pivoting around axis M1 and the secondary pivoting around axis M2 can be considered as a gimbal or gimballing motion of the therapeutic radiation head 210. For clarity of description, the primary pivoting around axis M1 may be referenced hereinbelow by the term "M1 pivot" or "M1 pivoting," and the secondary pivoting around axis M2 may be referenced hereinbelow by the term "M2 pivot" or "M2 pivoting." Notably, the terms primary/M1 and secondary/M2 are used herein for identification purposes and are not indicative of any particular imaging-related or treatment-related relative rankings. As illustrated in FIG. 2A, pivoting around the M2 axis allows for treatment radiation to be directed out of plane relative to the ring gantry plane 219.

For one preferred embodiment, the mount 206 and arm 207 are configured to allow controllable shortening and lengthening of the distance between the radiation treatment head 210 and the ring gantry 204. The arm 207 can be, for example, a telescoping arm. As such, the radial distance between the radiation treatment head 210 and the central longitudinal axis 214 is dynamically controllable. This capability can be advantageously used prevent collisions between the MLC 212 and the shielding structure 220 at locations along the central bore 218 when the radiation treatment head 210 is pivoted around the M2 pivot axis. In turn, this can advantageously relax certain design constraints, such allowing the central bore 218 to be larger than it would otherwise be while also allowing substantial M2-axis pivoting freedom of the radiation treatment head 210. In an alternative preferred embodiment (not shown), the radial distance between the radiation treatment head 210 and the central longitudinal axis 214 is fixed and not dynamically controllable.

Further illustrated in FIGS. 2A-2B is a first kV imaging system S1/D1 comprising an imaging source S1 and an imaging detector D1 coupled to the ring gantry 204 to be rotatable and translatable therewith. For another preferred embodiment (not shown), the first kV imaging system S1/D1 is translatable with the ring gantry 204 but is either fixably attached to the frame 202 or otherwise uncoupled with the rotations of the ring gantry 204. The first kV imaging system S1/D1 can generally have any of a variety of different hardware components (e.g., single x-ray source, source array, etc.) and two- or three-dimensional imaging schemes (e.g., 2D stereoscopic imaging, CBCT, tomosynthesis, etc.) without departing from the scope of the present teachings. For one preferred embodiment, the imaging source S1 comprises a source array that uses a computer-steerable electron beam and a spatial arrangement of metallic targets, such as one or more such devices developed by Triple Ring Technologies, supra, the imaging detector D1 is a digital array detector, and a 3D tomosynthesis in-treatment imaging functionality is provided.

The skilled artisan will appreciate that the IGRT system of FIGS. 2A-2B further includes a plurality of actuators of various types (not shown) for achieving the mechanical functionalities described hereinabove and hereinbelow in the instant disclosure. Thus, for example, the IGRT system includes respective actuation devices (not shown) to achieve the rotation of the ring gantry 204 around the rotation axis 214, the radial translation of the radiation treatment head 210 inwardly and outwardly from the central longitudinal axis 214, the M1 and M2 pivoting of the radiation treatment head 210, and the translation of the ring gantry structure 200 along the direction of the longitudinal axis. The IGRT system further includes one or more processing and/or control units, such as may be implemented on one or more programmable computers, for controlling the various actuators and sending signals to and from the various recited radiation sources and detectors as necessary to achieve the functionalities described hereinabove and hereinbelow in the instant disclosure. In view of the present disclosure, those skilled in the art would be able to configure such actuation devices, processing and/or control units, programmable computers, etc., and operate the described IGRT systems without undue experimentation.

FIGS. 3A-3B illustrate the IGRT system of FIGS. 2A-2B with annotations that more clearly depict the several degrees of freedom of the radiation treatment head 210 that are advantageously provided. In summary, the radiation treatment head 210 is rotatable around the central axis 214 (arrow 302), translatable along the longitudinal direction (arrow 304), pivotable around the M1 axis (arrow 306), pivotable around the M2 axis (arrow 308), and radially translatable relative to the central axis 214 (arrow 310). Advantageously, by virtue of the possibilities provided by the combination of these degrees of freedom, a rich variety of radiation treatment delivery plans are facilitated. At the same time, by virtue of a ring-style mechanical nature of the ring gantry 204, together with the fact that any cantilevered moments created along arm 207 at certain gantry angles are modest compared to those of conventional C-arm cantilevered moments, a high degree of mechanical stability is provided. Even further, a non-claustrophobic, "open-air" feel and experience is advantageously provided for the patient. Still further, as described further below, an ability is accommodated for keeping the patient completely stationary between the times of (i) pretreatment and/or setup imaging, and (ii) treatment delivery including in-treatment imaging.

Figure 4:
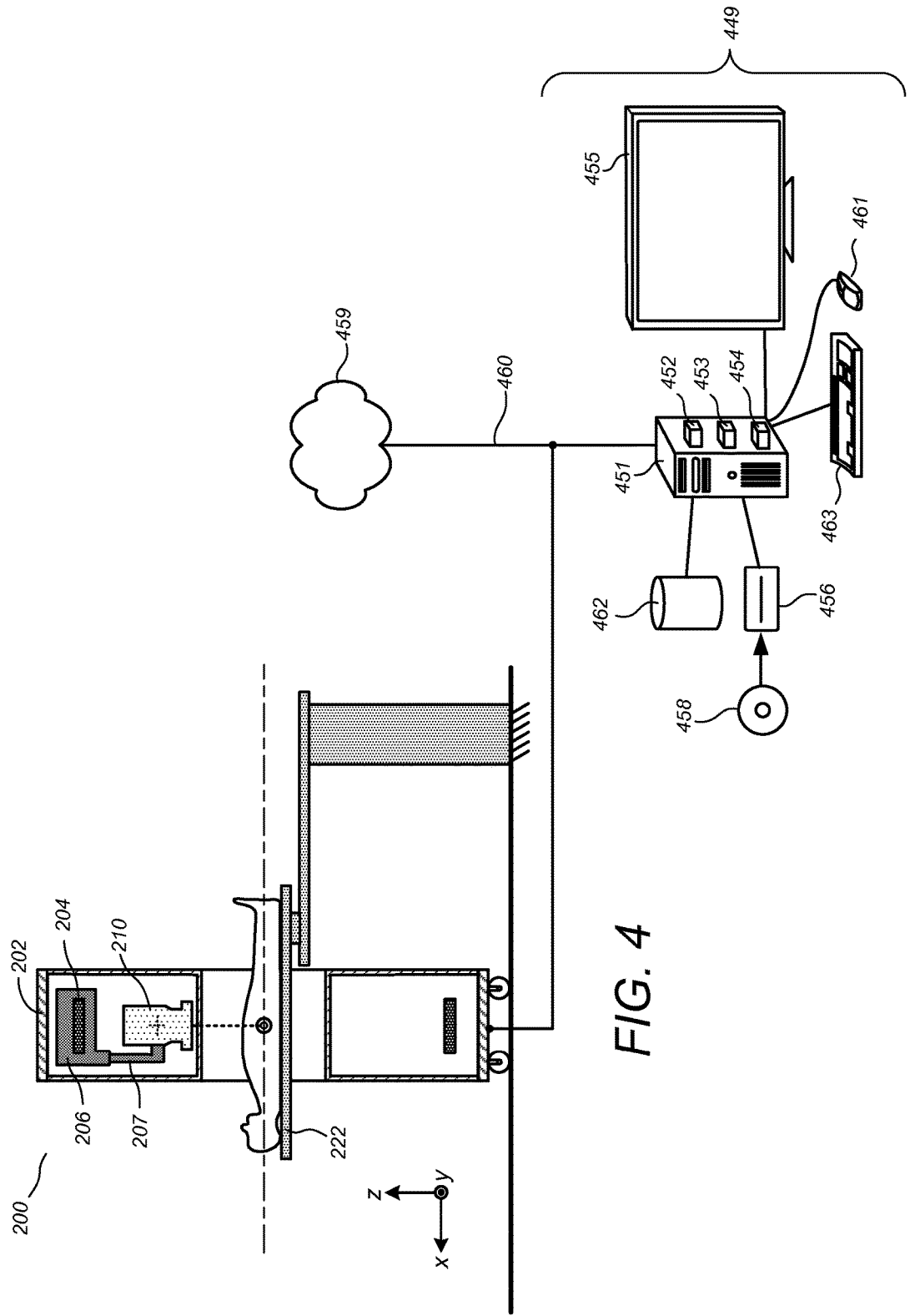
FIG. 4 illustrates a side cut-away view of an IGRT apparatus and a schematic diagram of a computer system integral therewith and/or coupled thereto according to a preferred embodiment.

FIG. 4 illustrates the ring gantry structure 200 as coupled to and/or integrated with a computer system 449 using one or more busses, networks, or other communications systems 460, including wired and/or wireless communications systems, and being capable in conjunction therewith of implementing the methods of one or more of the preferred embodiments. Methods of image guided radiation treatment in accordance with one or more of the preferred embodiments may be implemented in machine readable code (i.e., software or computer program product) and performed on computer systems such as, but not limited to, the computer system 449, wherein a central processing unit (CPU) 451 including a microprocessor 452, random access memory 453, and nonvolatile memory 454 (e.g., electromechanical hard drive, solid state drive) is operated in conjunction with various input/output devices, such as a display monitor 455, a mouse 461, a keyboard 463, and other I/O devices 456 capable of reading and writing data and instructions from machine readable media 458 such as tape, compact disk (CD), digital versatile disk (DVD), blu-ray disk (BD), and so forth. In addition, there may be connections via the one or more busses, networks, or other communications systems 460 to other computers and devices, such as may exist on a network of such devices, e.g., the Internet 459. Software to control the image guided radiation treatment steps described herein may be implemented as a program product and stored on a tangible storage device such as the machine readable medium 458, an external nonvolatile memory device 462, or other tangible storage medium. For clarity of presentation, the computer system 449 of FIG. 4 is omitted from further drawings and/or descriptions hereinbelow. Methods for configuring and programming the computer system 449 for achieving the functionalities described herein would be apparent to a person skilled in the art in view of the present disclosure.

FIGS. 5A-5D illustrate the IGRT system of FIGS. 2A-4 supra for different longitudinal positions of the ring gantry structure 200 (x(1), x(2), x(3), and x(4)) relative to the treatment vault. As illustrated, the distance between the radiation treatment head 210 and the ring gantry 204 can be varied to different amounts (d1, d2, d3, and d4, respectively) to avoid collisions between the MLC 212 and the shielding structure 220, and/or for other advantageous purposes. In a method for radiation treatment delivery according to a preferred embodiment, the IGRT apparatus is operated to apply non-coplanar radiation treatment, comprising rotating the radiation treatment head 210 around the longitudinal axis 214 to a plurality of different gantry angles, and translating the ring gantry structure 200 including ring gantry 204 to a plurality of different longitudinal positions along the longitudinal axis 214. At all times during the radiation treatment the patient can remain stationary relative to the treatment vault and does not need to be moved. The plurality of different longitudinal positions includes many for which the ring gantry plane 219 is not coincident with the isocenter (or, more generally, the treatment center), and for such positions the radiation treatment head 210 is pivoted to direct treatment radiation out of the ring gantry plane 219 and toward the treatment center, whereby conical non-coplanar radiation treatment and/or cono-helical non-coplanar radiation treatment can be delivered. During radiation treatment delivery, the radiation treatment head 210 can also be pivoted to direct treatment radiation off-center relative to the longitudinal axis 214 as may be needed for the particular treatment plan, motion compensation, and so forth.

Figure 14A:
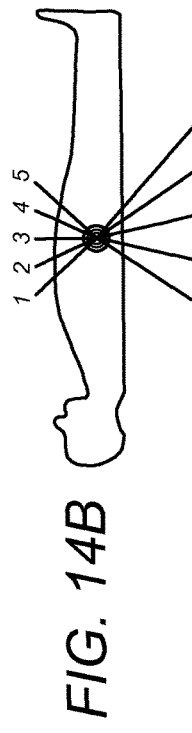
FIGS. 14A-14B illustrate examples of conical non-coplanar and cono-helical non-coplanar radiation treatment delivery using an IGRT system according to the method of FIGS. 5A-5D.
Figure 14B:
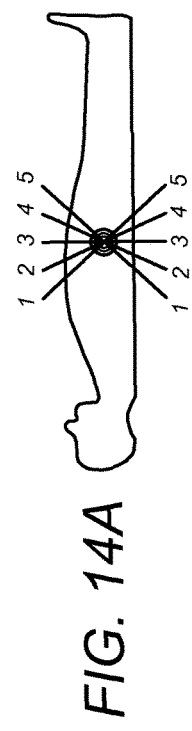

FIGS. 14A-14B illustrate non-coplanar rotational arc therapy profiles that can result from the operation of the IGRT apparatus as shown in FIGS. 5A-5D. In one preferred embodiment referenced herein as conical non-coplanar rotational arc therapy, the ring gantry 204 (and, therefore, the radiation treatment head 210) is longitudinally translated in discrete steps, with a rotation of the ring gantry 204 occurring at each step. There can be discrete firings of the therapeutic radiation beam at respective discrete gantry angles, or there can be continuous firings of the therapeutic radiation beam as the gantry angle is continuously changed, each of which are within the scope of the present teachings. FIG. 14A illustrates a cross-section of the resultant delivery profile for conical non-coplanar rotational arc therapy, with each discrete cone shape 1-5 corresponding to a different translational step of the radiation treatment head 210. In another preferred embodiment referenced herein as cono-helical non-coplanar rotational arc therapy, the ring gantry 204 (and, therefore, the radiation treatment head 210) is continuously translated in the longitudinal direction as the ring gantry 204 is rotated. There can be discrete firings of the therapeutic radiation beam at respective discrete gantry angles (and correspondingly discrete translational advances of the radiation treatment head 210), or there can be continuous firings of the therapeutic radiation beam as the gantry angle is continuously changed (and correspondingly continuous translational advances of the radiation treatment head 8210), each of which are within the scope of the present teachings. FIG. 14B illustrates a cross-section of the resultant delivery profile for cono-helical non-coplanar rotational arc therapy, which spans the same conical three-dimensional volume as conical non-coplanar rotational arc therapy, but which does so in a continuous or helical manner.

FIGS. 5E-5G illustrate side cut-away views of the IGRT apparatus of FIGS. 2A-4 for a plurality of different longitudinal positions of the ring gantry for what can be termed helical non-coplanar radiation treatment delivery, helical non-coplanar rotational arc therapy, or helical tomotherapy. The radiation treatment delivery provided in the example of FIGS. 5E-5G can achieve the same or substantially the same delivery profile as the helical tomotherapy provided by the HI-ART® treatment system commercially available from TomoTherapy Incorporated of Madison, Wis., while at the same time advantageously removing the need to move the patient. As illustrated in FIGS. 5E-5G, the ring gantry 204 is translated to different longitudinal positions for which the ring gantry plane 219 is not coincident with the isocenter (or, more generally, the treatment center), but for such positions the radiation treatment head 210 is not pivoted out of the ring gantry plane 219. There can be discrete firings of the therapeutic radiation beam at respective discrete gantry angles and correspondingly discrete translational advances of the radiation treatment head 210, or there can be continuous firings of the therapeutic radiation beam as the gantry angle is continuously changed and the radiation treatment head continuously advances. The resultant delivery profile (not shown) takes on a helical or spiral shape. Notably, any of the IGRT systems of the present disclosure would also, of course, be capable of delivering coplanar radiation treatment delivery or coplanar arc therapy by not using the ring gantry translation and/or ring gantry tilting capabilities described herein.

FIGS. 6A-6D illustrate an IGRT system according to a preferred embodiment that provides an ability to keep the patient completely stationary while achieving both (a) pretreatment and/or setup imaging of the target tissue volume using a high-quality 3D imaging device, and (b) delivery of radiation treatment to the target tissue volume by the radiation treatment head. As illustrated in FIGS. 6A-6D, the treatment vault of the IGRT system includes a 3D imaging device 602 (e.g., CT, MRI) separate from the ring gantry structure 200 containing the ring gantry 204 and radiation treatment head 210. The 3D imaging device 602 is translatable, such as by a translation mechanism 604, along the central longitudinal axis 214 separately and independently of the ring gantry structure 200. The ring gantry structure 200 is translatable along the central longitudinal axis 214 between a first location L1 for which it longitudinally encompasses the isocenter 216 and a second location L2 away from the isocenter. Similarly, the 3D imaging device 602 is translatable along the central longitudinal axis 214 between a third location L3 away from the isocenter and a fourth location L4 for which it longitudinally encompasses the isocenter. For pre-treatment and/or setup imaging, the ring gantry structure is moved out of the way while the 3D imaging device acquires the pre-treatment and/or setup images (FIGS. 6A-6B), while for delivery of radiation treatment the 3D imaging device is moved out of the way to allow the ring gantry-mounted radiation treatment head to perform radiation delivery (FIGS. 6C-6D), all without needing to translate, rotate, or otherwise move the patient. The skilled artisan will appreciate that any of a variety of different mechanical translation schemes and mounting schemes can be used achieving the translation functionality of the 3D imaging device (e.g., ceiling rails, wall rails, floor rails, etc.)

Figure 7:
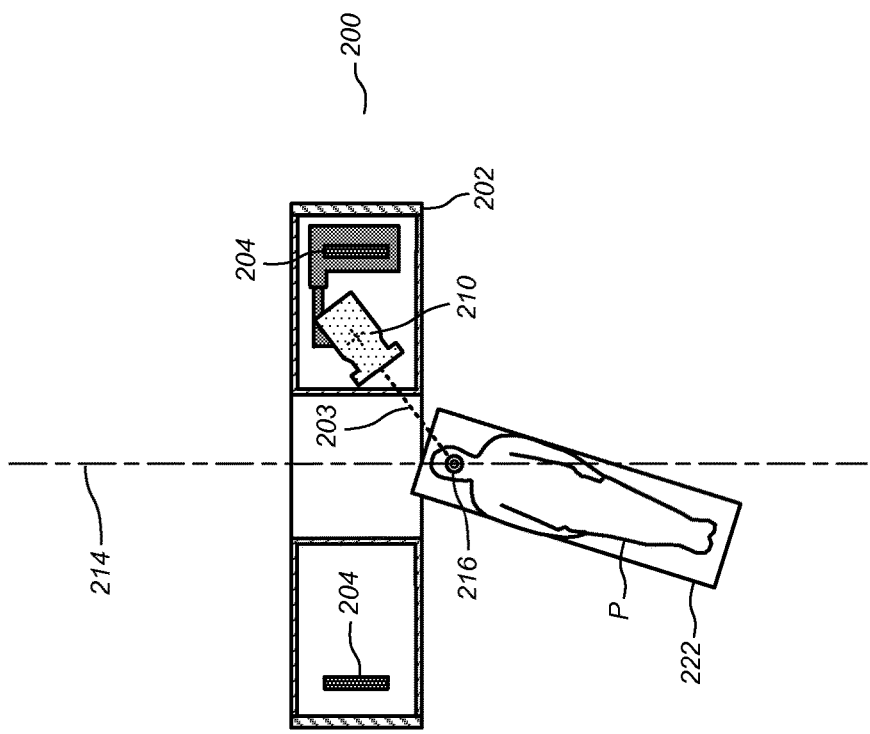
FIG. 7 illustrates a top cut-away view of an IGRT apparatus according to a preferred embodiment during an optional couch kick mode of operation.

FIG. 7 illustrates using a so-called "couch kick" (varying the angle of the patient couch 222 relative to the longitudinal axis 214) in an optional mode of operation particularly useful for certain cranial treatments. Advantageously, a wide variety of orientations and configurations are made available for directing radiation beams into the head at various angles of attack.

Figure 8B:
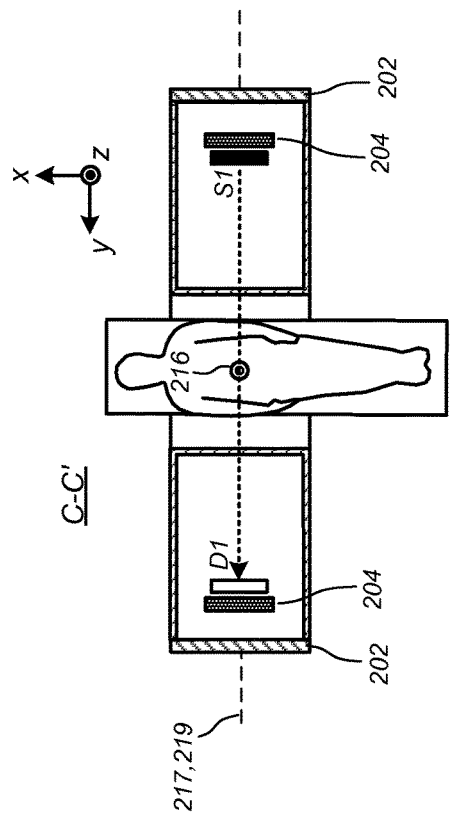
FIGS. 8A-8B illustrate axial and top cut-away views, respectively, of an IGRT apparatus according to a preferred embodiment.
Figure 8A:
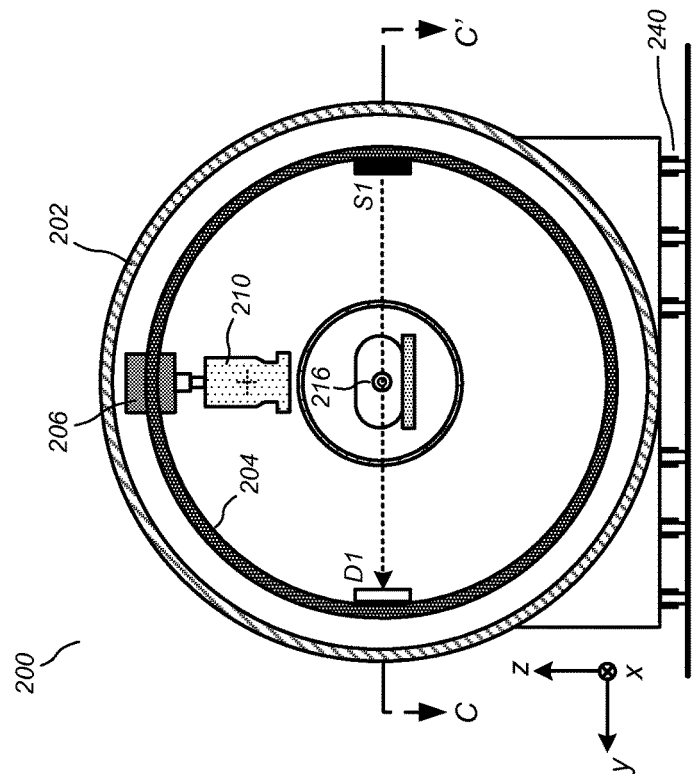

FIG. 8A illustrates the same side cross-sectional view of the ring gantry structure 200 of FIG. 2B, supra, while FIG. 8B illustrates a top cross-sectional view (i.e., a cross-sectional view as seen from the ceiling of the treatment vault) of the ring gantry structure 200. Included in the preferred embodiment of FIG. 8A is a first kV imaging system S1/D1 that is mounted on the ring gantry 204 and is therefore rotatable and translatable therewith. Notably, if the ring gantry structure 200 is translated such that the ring gantry plane is away from the isocenter 216, then the first kV imaging system S1/D1 will likewise no longer be directed toward imaging at the isocenter 216.

FIGS. 9A-9C and FIG. 10 illustrate IGRT systems according to alternative preferred embodiments, wherein in-treatment imaging at the isocenter 216 can still be achieved even where the ring gantry plane 219 is positioned off-isocenter. A second kV imaging system D2/S2 including a second imaging source S2 and a second imaging detector D2 are provided. The second kV imaging system D2/S2 is configured for imaging at the isocenter 216 and is fixed relative to the treatment vault using the fixed imaging mounts 952 and 954. As illustrated in FIG. 9C, when the ring gantry structure 200 is moved longitudinally such that the ring gantry plane 219 is removed from the transverse isocentric plane 217, the second kV imaging system D2/S2 can "take over" for the first kV imaging system D1/S1 to provide the necessary in-treatment image information. In an alternative preferred embodiment, the second kV imaging system S2/D2 can be movable in the longitudinal direction relative to the treatment vault independently of the ring gantry structure 200. As illustrated in another preferred embodiment shown in FIG. 10, a second kV imaging system can take on any of a variety of different configurations, such as the use of dual source arrays S2*a*/S2*b* mounted on fixed pads 952*a*/952*b* and dual detector arrays D2*a*/D2*b* mounted on fixed pads 954*a*/954*b* in a stereoscopic configuration. In an alternative preferred embodiment, the second kV imaging system can be movable relative to the treatment vault in any of a variety of different ways while remaining uncoupled with the longitudinal movement of the ring gantry structure 200, for the purpose of obtaining a better configuration for in-treatment imaging at the isocenter 216.

FIGS. 11A-11C illustrate side cut-away views of an IGRT apparatus including a ring gantry tilted around a horizontal tilt axis at different respective tilt angles according to a preferred embodiment. IGRT apparatus 1100 includes a ring gantry structure 1102 including a ring gantry 1104. The ring gantry structure 1102 and ring gantry 1104 are coupled such that they are jointly tiltable (and/or translatable) and therefore such tilting (or translation) is described hereinbelow for the ring gantry only, it being understood that the ring gantry structure 1102 will so tilt (and/or translate) with the ring gantry 1104. The ring gantry 1104 has a central opening sufficiently large to accommodate a body of a patient positioned along a longitudinal axis 1114 and extending therethrough. A gantry tilting mechanism 1170/1172 is provided that is configured to tilt the ring gantry 1104 around a horizontal tilt axis 1177 to a plurality of different tilt angles relative to the longitudinal axis 1114. The ring gantry 1104 defines a ring gantry plane 1119. A radiation treatment head 1110 is coupled to the ring gantry 1104 and is rotatable around a center of the ring gantry plane 1119 in at least a 180 degree arc, and preferably a 360 arc. The radiation treatment head 1110 is mechanically coupled to the ring gantry such that a distance "d" by which the radiation treatment head extends inwardly toward the central opening relative to the ring gantry is dynamically controllable, with the distance "d" being d1 for the tilt of FIG. 11A, d2 for the non-tilted scenario of FIG. 11B, and d3 for the tilt of FIG. 11C. The mechanical coupling can be based, for example, on the use of a telescoping arm 1107 of a mount 1106 that is connected to the ring gantry 1104. Preferably, the radiation treatment head 1110 is coupled to the telescoping arm 1107 in a manner that allows pivoting around multiple pivot axes such that treatment radiation can be directed off-center relative to the longitudinal axis 1114 and/or out-of-plane relative to the ring gantry plane 1119.

The skilled artisan will appreciate that the IGRT system 1100 of FIGS. 11A-11C further includes a plurality of actuators of various types (not shown) for achieving the mechanical functionalities described hereinabove and hereinbelow in the instant disclosure. For example, the gantry tilting mechanism 1170/1172 includes a raisable, lowerable, and translatable floor pivot structure 1170 configured to operate in unison with a lowerable, raisable, and translatable ceiling pivot structure 1172 for achieving the described tilting functionality around the horizontal tilt axis 1177. The IGRT system further includes one or more processing and/or control units, such as may be implemented on one or more programmable computers, for controlling the various actuators and sending signals to and from the various recited radiation sources and detectors as necessary to achieve the functionalities described hereinabove and hereinbelow in the instant disclosure. In view of the present disclosure, those skilled in the art would be able to configure such actuation devices, processing and/or control units, programmable computers, etc., and operate the described IGRT systems without undue experimentation.

FIGS. 12A-12C illustrate in-plane cut-away views of the IGRT apparatus of FIGS. 11A-11C when viewed in the ring gantry plane 1119 for each of the respective ring gantry tilt angles thereof. Included in each of FIGS. 12A-12C are views of the radiation treatment head 1110 at two different gantry angles for illustrating the preferred dynamic inward/outward position control of the radiation treatment head 1110 relative to the ring gantry 1104. According to a preferred embodiment, the distance "d" by which the radiation treatment head 1110 extends inwardly from the ring gantry 1104 as the radiation treatment head 1110 is rotated through a plurality of gantry angles is dynamically controlled such that the radiation treatment head 1110 is maintained adjacently outside a predefined cylindrical buffer zone 1118 ("no-fly zone") extending around and along the longitudinal axis 1114. As illustrated in FIGS. 12A and 12C, when the ring gantry 1104 is tilted to an off-normal tilt angle relative to the longitudinal axis 1114, the in-gantry-plane trajectory of the radiation treatment head 1110 is elliptical (see ellipses eA and eC, respectively) in order to be maintained at or just outside the cylindrical buffer zone 1118. For embodiments (not shown) in which a central bore shield is provided, the cylindrical buffer zone 1118 corresponds to the outer dimensions of the center bore shield. In one preferred embodiment, the IGRT system 1100 is configured to achieve a ring gantry tilt angle of at least 30 degrees while maintaining a suitably sized cylindrical buffer zone 1118. In another preferred embodiment, the IGRT system 1100 is configured to achieve a ring gantry tilt angle of at least 45 degrees while maintaining a suitably sized cylindrical buffer zone 1118, and in still another preferred embodiment is configured to achieve a ring gantry tilt angle of at least 60 degrees while maintaining a suitably sized cylindrical buffer zone 1118.

Notably, although U.S. Pat. No. 7,188,999B2 discusses one proposal that could at least partially address the problem of maintaining some sort of no-fly zone around the patient when the arc-shaped guide rail is tilted off-normal relative to the longitudinal axis, that proposal is to actuably elevate the entire gantry structure, including the entire arc-shaped guide rail, to different elevations above the floor of the treatment room. In addition to requiring the mechanical actuation of a very heavy load including the combined weight of the arc-shaped guide rail and the LINAC, and in addition to the arc-shaped guide rail being only semicircular in the context of the gantry-elevating proposal of U.S. Pat. No. 7,188,999B2, thereby limiting the potential positioning of the LINAC to some portion of a rising and falling half-sphere, there are further practical limitations on the allowed range of LINAC positioning when compared to preferred embodiments of FIGS. 11A-11C and FIGS. 13A-13C.

The horizontal tilt axis 1177 is generally normal to the longitudinal axis 1114. For one preferred embodiment, which is illustrated in FIGS. 11A-11C, the longitudinal axis 1114 passes through an isocenter 1116 (or, more generally, a treatment center). For one preferred embodiment, the gantry tilting mechanism 1170/1172 can be configured to also serve as a gantry translation mechanism capable of translating the entire ring gantry 1104 in a direction of a the longitudinal axis. For this case, the horizontal tilt axis 1177 is likewise correspondingly movable in the longitudinal direction.

Also provided in conjunction with the IGRT system 1100 of FIGS. 11A-11C, as well as the IGRT system 1300 of FIGS. 13A-13C infra are one or more kV imaging systems analogous to those illustrated in FIGS. 8A-10 and described in the context of the IGRT systems of FIGS. 2A-5G, which description need not be repeated here. Additionally, for preferred embodiments in which the ring gantry 1104/1304 is translatable along the direction of the longitudinal axis 1114/1314, the treatment vault can be outfitted with an independently translatable 3D imaging system and with a separate 3D imaging device (e.g., CT, MRI) translatable along the longitudinal axis separately and independently of the ring gantry structure, for providing the ability to keep the patient completely stationary while achieving both (i) pre-treatment and/or setup imaging, and (ii) delivery of radiation treatment, in a manner analogous to that illustrated in FIGS. 6A-6D and described in the context of the IGRT systems of FIGS. 2A-5G, which description need not be repeated here.

FIGS. 13A-13C illustrate top cut-away views of an IGRT apparatus 1300 according to a preferred embodiment, the IGRT apparatus 1300 having similar capabilities as the IGRT apparatus 1100 of FIG. 11, supra, except that the ring gantry is tiltable around a vertical axis rather than a horizontal axis. IGRT apparatus 1300 includes a ring gantry structure 1302 including a ring gantry 1304 having has a central opening sufficiently large to accommodate a body of a patient positioned along a longitudinal axis 1314 and extending therethrough. A gantry tilting mechanism (not shown) is provided that is configured to tilt the ring gantry 1304 around a vertical tilt axis 1377 to a plurality of different tilt angles relative to the longitudinal axis 1114. Similar to the preferred embodiment of FIGS. 11A-11C, a radiation treatment head 1310 is coupled to the ring gantry 1304 and is rotatable around a center of a ring gantry plane 1319, and is mechanically coupled to the ring gantry 1304 such that a distance "d" by which the radiation treatment head extends inwardly toward the central opening relative to the ring gantry is dynamically controllable, with the distance "d" being d1 for the tilt of FIG. 13A, d2 for the non-tilted scenario of FIG. 13B, and d3 for the tilt of FIG. 13C. The mechanical coupling can be based, for example, on the use of a telescoping arm 1307 of a mount 1306 that is connected to the ring gantry 1304. Preferably, the radiation treatment head 1310 is coupled to the telescoping arm 1307 in a manner that allows pivoting around multiple pivot axes such that treatment radiation can be directed off-center relative to the longitudinal axis 1314 and/or out-of-plane relative to the ring gantry plane 1319. The vertical tilt axis 1377 is generally normal to the longitudinal axis 1314. For one preferred embodiment, which is illustrated in FIGS. 13A-11C, the longitudinal axis 1314 passes through an isocenter 1316 (or, more generally, a treatment center). For one preferred embodiment, the gantry tilting mechanism (not shown) can be configured to also serve as a gantry translation mechanism capable of translating the entire ring gantry 1304 in a direction of a the longitudinal axis, and for such case the vertical tilt axis 1377 is likewise correspondingly movable in the longitudinal direction.

A method for image guided radiation treatment of a body part of a patient based on the IGRT system 1100 (horizontal tilt) or 1300 (vertical tilt) can proceed as follows. The patient is positioned along a longitudinal axis 1114/1314 of the IGRT apparatus 1100/1300. The IGRT apparatus is operated to apply non-coplanar radiation treatment to the body part during a treatment fraction, the operating comprising rotating the radiation treatment head 1110/1310 to a plurality of different gantry angles, the operating further comprising tilting the ring gantry 1104/1304 to a plurality of different tilt angles relative to the longitudinal axis 1114/1314. For any particular non-normal tilt angle of the ring gantry 1104/1304, as the radiation treatment head 1110/1310 is rotated through different gantry angles, the distance by which the radiation treatment head 1110/1310 extends inwardly is dynamically controlled such that the radiation treatment head 1110/1310 is maintained adjacently outside a predefined cylindrical buffer zone 1118/1318 extending around the patient along the longitudinal axis.

The predefined cylindrical buffer zone 1118/1318 can be a circularly cylindrical shape, an elliptically cylindrical shape, or alternatively there can be provided a buffer zone around the patient that has any of a variety of different shapes, including shapes that vary with distance along the longitudinal axis. Optionally, the radiation treatment head 1110/1310 can be pivoted around at least two pivot axes such that treatment radiation can be directed out of the ring gantry plane 1119/1319 and/or directed off-center relative to the longitudinal axis 1114/1314 as may be needed for the particular treatment plan, motion compensation, and so forth.

Figure 15A:
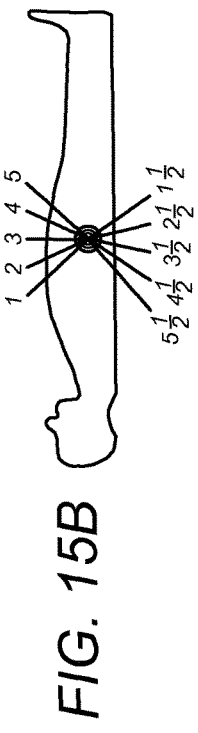
FIGS. 15A-15B illustrate examples of non-coplanar radiation treatment delivery using the IGRT system of FIGS. 11A-11C.
Figure 16A:
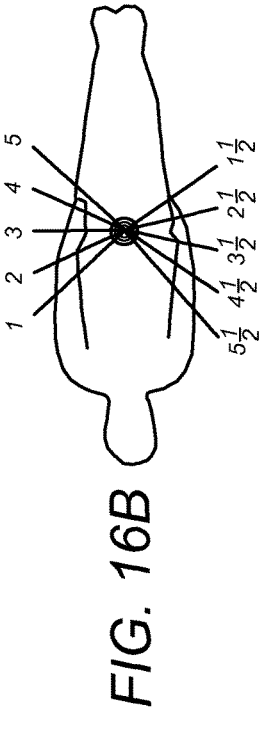
FIGS. 16A-16B illustrate examples of non-coplanar radiation treatment delivery using the IGRT system of FIGS. 13A-13C.
Figure 15B:
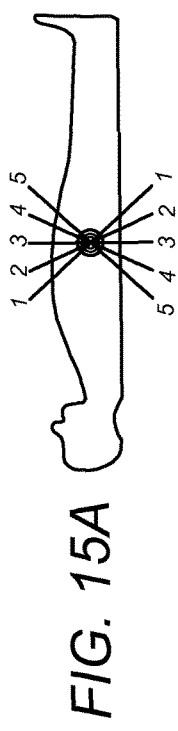
Figure 16B:
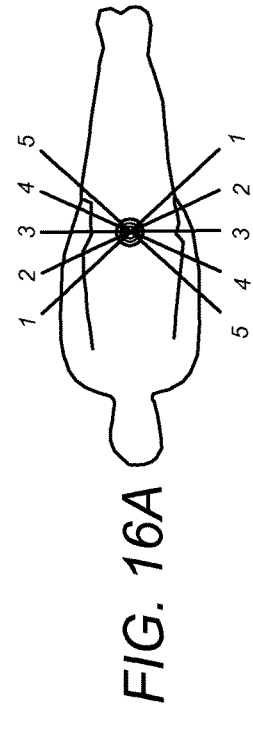

FIGS. 15A-15B illustrate examples of non-coplanar radiation treatment delivery using the IGRT system 1100 of FIGS. 11A-11C, while FIGS. 16A-16B illustrate examples of non-coplanar radiation treatment delivery using the IGRT system 1300 of FIGS. 13A-13C. To achieve the profiles of FIGS. 15A and 16A, the gantry angle is actuated (in discrete steps or continuously) through one full rotation for each discrete ring gantry tilt angle (horizontal tilt angle and vertical tilt angle, respectively, for FIGS. 15A and 16A). To achieve the profiles of FIGS. 15A and 16A, the tilt angle is progressively varied (in discrete steps or continuously) as the gantry angle is actuated (in discrete steps or continuously) through successive rotations.

More generally, a rich variety of radiation therapy profiles and strategies can be accommodated using one or more of the presently disclosed IGRT systems. Such possibilities include, but are not limited to: single or parallel opposed static beams with rectangular field shaping and 1D (wedge or virtual wedge using MLC) intensity modulation; static beams with rectangular field shaping and 1D modulation; coplanar rotational treatments ("arc therapy") with rectangular field shaping and 1D modulation; coplanar or non-coplanar beams with irregular field shaping and 1D modulation ("conformal radiation therapy" or CRT); coplanar or non-coplanar beams with irregular field shaping and 2D modulation ("intensity modulated radiation therapy" or IMRT); and tomotherapy (helical or sequential) with coplanar rotation using a narrow beam in combination with couch movement and 2D modulation. Such possibilities further include rotational arc therapy, also called intensity modulated arc therapy (IMAT), including one or more coplanar rotations, irregular field shaping, and 2D modulation, with gantry rotation speed, dose rate, MLC positions, and in some cases collimator angles being varied during rotation, and including multiple rotations that increase the achievable degree of intensity modulation in view of practical constraints on MLC motion during treatment.

Provided according to another preferred embodiment is an IGRT system (not shown) that is similar to that of FIGS. 2A-3B, including a radiation treatment head movably coupled to a circular ring gantry in a manner that allows extension toward and retraction away from the central longitudinal axis (see arrow 310 in FIG. 3B), such as by a telescoping arm coupling, but wherein the x-axis translation ability of the ring gantry is omitted. Although being somewhat less versatile than the preferred embodiment of FIGS. 2A-3B because of the lack of longitudinal translation ability, such device would be simpler and less expensive to realize, while also providing several advantages over known prior art ring gantry systems by virtue of the extendibility and retractibility of the radiation treatment head relative to the outer perimeter of the ring gantry. For example, the radiation treatment head will be able to traverse any of a variety of different circular and non-circular trajectories for achieving any of a variety of different goals. The ability to adjust the source-axis distance (SAD) allows an advantage of being able to adjust the radiation treatment field size, which changes proportionally to distance, as well as the effective dose rate (in MU/min) at the target location. With regard to field size, there are often practical limitations for how small that field size can get by collimation, and the ability to make the SAD smaller can help alleviate this difficulty. For example, in certain practical scenarios it could be found difficult to achieve a field size of less than 5 mm at an SAD of 800 mm (for example, commissioning difficulties because it is very hard to measure small field dosimetry parameters such as profile and output factor for such field sizes). However, with a variable SAD, a system could be commissioned with a collimator that is 5 mm at 800 mm SAD, and then for a treatment session for which a smaller field size of 4 mm is desired, the SAD could be changed to 640 mm to achieve the desired field size (5 mm×640/800=4 mm). This can be useful when treating small targets, e.g., the trigeminal nerve root, which is a target in the treatment of trigeminal neuralgia. Conversely, where a larger field size is desired than can be provided by a relatively small MLC (e.g., a 10 cm×12 cm MLC), this can be achieved by moving the radiation treatment head further away. The ability to actuably vary the SAD can also be useful for accommodating obese patients or adjusting for very thin patients. The ability to dynamically vary the SAD during gantry rotation can also be advantageously useful for accommodating "couch kicks" or other orientations in which the patient's body is not perpendicular to the ring gantry plane, for which cases elliptical orbits or other non-circular orbits may advantageously allow for the possibility of such orientations and a variety of additional associated non-coplanar delivery angles for the gantry-based system.

Whereas many alterations and modifications of the present invention will no doubt become apparent to a person of ordinary skill in the art after having read the foregoing description, it is to be understood that the particular embodiments shown and described by way of illustration are in no way intended to be considered limiting. By way of example, it is to be understood that while dynamic control of the inward/outward extension of the radiation treatment head is indeed particularly advantageous when that control is applied during a treatment fraction as the gantry is rotated (either continuously or in discrete steps), the dynamic control of the radiation treatment head is not limited as such, and therefore in some preferred embodiments such dynamic control can be applied just once (e.g., prior to treatment delivery, or during one of the treatment fractions before commencing gantry rotation and/or beam activation, for example to accommodate an obese patient) while remaining within the scope of the present teachings and while still constituting dynamic control as that term is used herein. By way of further example, although one or more preferred embodiments are described above in which the in-therapy imaging sources are distinct from the therapeutic radiation source, in other preferred embodiments the imaging system can be provided as a portal imaging system, in which an imaging detector is provided opposite the therapeutic radiation source relative to the isocenter.

By way of further example, while variation of the gantry angle is described in one or more preferred embodiments supra as being achieved by rotating the ring gantry itself, whereby the radiation treatment head rotates by virtue of its connection to the ring gantry by a fixed mechanical mount, the scope of the preferred embodiments is not so limited. It is not outside the scope of the present teachings, for example, to instead provide a non-rotating ring gantry, wherein the gantry angle is varied by mechanical translation of the mount that holds the radiation treatment head around the circumference of the ring gantry. Therefore, reference to the details of the embodiments are not intended to limit their scope, which is limited only by the scope of the claims set forth below.

What is claimed is:

1. A radiation treatment apparatus, comprising:
a ring gantry having a central opening;
a radiation treatment head coupled to said ring gantry and rotatable around said central opening in at least a 180 degree arc; and
a gantry translation apparatus coupled with the ring gantry to translate said ring gantry in a direction of a longitudinal axis extending through said central opening, said radiation treatment apparatus to provide radiation treatment to a target tissue volume of a patient disposed at an isocenter of a treatment vault, the radiation treatment apparatus further comprising:
a ring gantry structure within which said ring gantry is housed, said ring gantry structure being translatable along said longitudinal axis between (i) a first location for which the ring gantry structure longitudinally encompasses the isocenter, and (ii) a second location for which the ring gantry structure does not encompass the isocenter; and
a 3D imaging device distinct from said ring gantry structure to provide at least one of pre-treatment imaging and setup imaging of the target tissue volume, wherein said 3D imaging device is translatable along said longitudinal axis between (iii) a third location for which the 3D imaging device does not longitudinally encompass the isocenter, and (iv) a fourth location for which the 3D imaging device encompasses the isocenter;
wherein both (a) pre-treatment or setup imaging of the target tissue volume by the 3D imaging device, and (b) delivery of radiation treatment to the target tissue volume by the radiation treatment head can be achieved without requiring movement of the patient.

2. The radiation treatment apparatus of claim 1, wherein said radiation treatment head is rotatable around said central opening in at least a 360 degree arc.

3. The radiation treatment apparatus of claim 1, said ring gantry defining a central ring gantry plane, wherein said radiation treatment head is coupled to said ring gantry in a manner that allows pivoting of the radiation treatment head around at least one pivot axis such that treatment radiation can be directed out of plane relative to said ring gantry plane.

4. The radiation treatment apparatus of claim 3, wherein said radiation treatment head is coupled to said ring gantry in a manner that maintains a center of mass of the radiation treatment head along the central ring gantry plane for any pivot angle of the radiation treatment head around the at least one pivot axis.

5. The radiation treatment apparatus of claim 3, said longitudinal axis being a central longitudinal axis passing through said isocenter, wherein said radiation treatment head is coupled to said ring gantry in a manner that allows pivoting of the radiation treatment head around at least two pivot axes such that treatment radiation can further be directed off-center relative to said central longitudinal axis.

6. The radiation treatment apparatus of claim 1, wherein said pre-treatment or setup imaging comprises translating said ring gantry structure to said second location and translating said 3D imaging device to said fourth location, and wherein said delivery of radiation treatment comprises translating said 3D imaging device to said third location and translating said ring gantry structure to said first location.

7. The radiation treatment apparatus of claim 1, wherein said 3D imaging device is selected from the group consisting of: a CT imaging device, and an MRI device.

* * * * *